United States Patent
Tajima

(10) Patent No.: US 10,822,646 B2
(45) Date of Patent: Nov. 3, 2020

(54) REACTION CONTAINER CONTROL SYSTEM

(71) Applicant: UNIVERSAL BIO RESEARCH CO., LTD., Matsudo-Chi, Chiba (JP)

(72) Inventor: Hideji Tajima, Matsudo (JP)

(73) Assignee: Universal Bio Research Co., Ltd. (JP)

( * ) Notice: Subject to any disclaimer, the term of this patent is extended or adjusted under 35 U.S.C. 154(b) by 42 days.

(21) Appl. No.: 15/263,483

(22) Filed: Sep. 13, 2016

(65) Prior Publication Data

US 2017/0058323 A1 Mar. 2, 2017

Related U.S. Application Data

(62) Division of application No. 13/983,508, filed as application No. PCT/JP2012/052632 on Feb. 6, 2012, now Pat. No. 9,481,906.

(30) Foreign Application Priority Data

Feb. 4, 2011 (JP) .................. 2011-023378

(51) Int. Cl.
*C12Q 1/68* (2018.01)
*G01N 21/13* (2006.01)
(Continued)

(52) U.S. Cl.
CPC ........... *C12Q 1/686* (2013.01); *C12Q 1/6848* (2013.01); *G01N 21/13* (2013.01); *G01N 21/31* (2013.01);
(Continued)

(58) Field of Classification Search
CPC ...... C12Q 1/686; C12Q 1/6848; G01N 21/13; G01N 21/31; G01N 21/6428;
(Continued)

(56) References Cited

U.S. PATENT DOCUMENTS 3,918,793 A   11/1975   Kraft
4,626,684 A   12/1986   Landa
(Continued)

FOREIGN PATENT DOCUMENTS

CN   201281708 Y   7/2009
GB   2441833 A   3/2008
(Continued)

OTHER PUBLICATIONS

International Search Report for PCT/JP2012/052632 by ISA/JP, and English translation, dated May 1, 2012.
(Continued)

*Primary Examiner* — Benjamin R Whatley
(74) *Attorney, Agent, or Firm* — Andrus Intellectual Property Law, LLP

(57) ABSTRACT

A reaction container control system including a reaction container, a sealing lid, a temperature control block, and a heater. The reaction container includes a lower side wall section, an upper side wall section, and an aperture. The sealing lid seals the reaction container by fitting to the aperture of the reaction container. When the sealing lid is fitted to the aperture, light based on an optical state within the reaction container is receivable by a measuring device via the sealing lid. The temperature control block contacts or extends adjacent the lower side wall section, and includes a temperature source operable to increase or decrease a temperature inside the reaction container. The heater contacts or extends adjacent the upper side wall section, and includes a heat source operable to heat the reaction container to prevent condensation on the sealing lid fitted to the aperture.

2 Claims, 14 Drawing Sheets

(51) Int. Cl.

| | | |
|---|---|---|
| *C12Q 1/686* | (2018.01) | |
| *G01N 35/10* | (2006.01) | |
| *G01N 21/64* | (2006.01) | |
| *G01N 35/00* | (2006.01) | |
| *G01N 21/31* | (2006.01) | |
| *C12Q 1/6848* | (2018.01) | |
| *B01L 7/00* | (2006.01) | |

(52) U.S. Cl.
CPC ..... *G01N 21/6428* (2013.01); *G01N 21/6452* (2013.01); *G01N 35/0098* (2013.01); *G01N 35/10* (2013.01); *G01N 35/1065* (2013.01); *B01L 7/52* (2013.01); *B01L 7/54* (2013.01); *B01L 2300/1805* (2013.01); *G01N 2021/6421* (2013.01); *G01N 2021/6439* (2013.01); *G01N 2035/00366* (2013.01); *G01N 2035/00376* (2013.01); *G01N 2035/103* (2013.01); *G01N 2035/1076* (2013.01); *G01N 2201/08* (2013.01); *G01N 2203/0226* (2013.01)

(58) Field of Classification Search
CPC .......... G01N 21/6452; G01N 35/0098; G01N 35/1065; G01N 2021/6421; G01N 2021/6439; G01N 2035/103; G01N 2035/1076; G01N 2035/00376; G01N 2035/00366; G01N 2201/08; G01N 2203/0226; B01L 2300/1805; B01L 7/52; B01L 7/54

See application file for complete search history.

(56) References Cited

U.S. PATENT DOCUMENTS

| | | | |
|---|---|---|---|
| 4,944,922 A | 7/1990 | Hayashi | |
| 5,290,513 A | 3/1994 | Berthold et al. | |
| 5,589,351 A | 12/1996 | Harootunian | |
| 5,846,489 A | 12/1998 | Bienhaus et al. | |
| 5,895,631 A | 4/1999 | Tajima | |
| 6,043,880 A | 3/2000 | Andrews et al. | |
| 6,143,250 A | 11/2000 | Tajima | |
| 6,372,183 B1 | 4/2002 | Akong et al. | |
| 6,509,193 B1 | 1/2003 | Tajima | |
| 2002/0179849 A1 | 12/2002 | Maher | |
| 2003/0106682 A1* | 6/2003 | Reid | B01L 7/52 165/206 |
| 2003/0127609 A1 | 7/2003 | El-Hage | |
| 2003/0162285 A1 | 8/2003 | Tajima | |
| 2004/0038390 A1 | 2/2004 | Boege et al. | |
| 2004/0224317 A1 | 11/2004 | Kordunsky et al. | |
| 2004/0241872 A1 | 12/2004 | Wegrzyn et al. | |
| 2004/0258563 A1 | 12/2004 | Young et al. | |
| 2004/0259091 A1 | 12/2004 | Yasuda et al. | |
| 2005/0151972 A1 | 7/2005 | Boege et al. | |
| 2005/0213868 A1 | 9/2005 | Cunningham | |
| 2006/0012130 A1 | 1/2006 | Vann et al. | |
| 2006/0093254 A1 | 5/2006 | Mozdy | |
| 2007/0009392 A1 | 1/2007 | Tajima et al. | |
| 2007/0114444 A1 | 5/2007 | Reid | |
| 2008/0188725 A1 | 8/2008 | Markle et al. | |
| 2008/0248586 A1 | 10/2008 | Tajima | |
| 2008/0274511 A1 | 11/2008 | Tan | |
| 2009/0189089 A1 | 7/2009 | Bedingham et al. | |
| 2009/0221080 A1 | 9/2009 | Tajima | |
| 2009/0263782 A1 | 10/2009 | Ward et al. | |
| 2010/0137165 A1 | 6/2010 | Tajima | |
| 2010/0163111 A1 | 7/2010 | Tajima | |
| 2010/0209298 A1 | 8/2010 | Kalra | |
| 2010/0236324 A1 | 9/2010 | Tajima et al. | |
| 2010/0273245 A1 | 10/2010 | Tajima | |
| 2011/0183378 A1* | 7/2011 | Takagi | C12Q 1/686 435/91.2 |
| 2011/0236960 A1 | 9/2011 | Bird | |
| 2012/0122231 A1* | 5/2012 | Tajima | G01N 35/026 436/164 |
| 2012/0164649 A1 | 6/2012 | Smethers | |
| 2012/0270309 A1* | 10/2012 | Arai | B01L 7/52 435/303.1 |

FOREIGN PATENT DOCUMENTS

| | | | | |
|---|---|---|---|---|
| JP | H11271227 A | 10/1999 | | |
| JP | 2009092420 A | 4/2009 | | |
| WO | WO 03/098278 A2 | 11/2003 | | |
| WO | WO 2008/011875 A1 | 1/2008 | | |
| WO | WO-2010140680 A1 * | 12/2010 | .......... G01N 35/026 | |
| WO | WO 2010140680 A1 | 12/2010 | | |
| WO | WO-2011021640 A1 * | 2/2011 | ............... B01L 7/52 | |

OTHER PUBLICATIONS

Written Opinion for PCT/JP2012/052632 by ISA/JP, dated May 1, 2012.
International Preliminary Examination Report for PCT/JP2012/052632, by IPEA/JP, dated Jun. 3, 2013.
Requirement for Restriction/Election dated Jul. 28, 2015, in U.S. Appl. No. 13/983,508 (6 pages).
Non-Final Rejection dated Oct. 21, 2015 in U.S. Appl. No. 13/983,508 (20 pages).
Notice of Allowance dated Jun. 15, 2016, in U.S. Appl. No. 13/983,508 (10 pages).
Supplemental European Search Report received in European Application No. 12742612.0, dated Feb. 9, 2018, 4 pages.

* cited by examiner

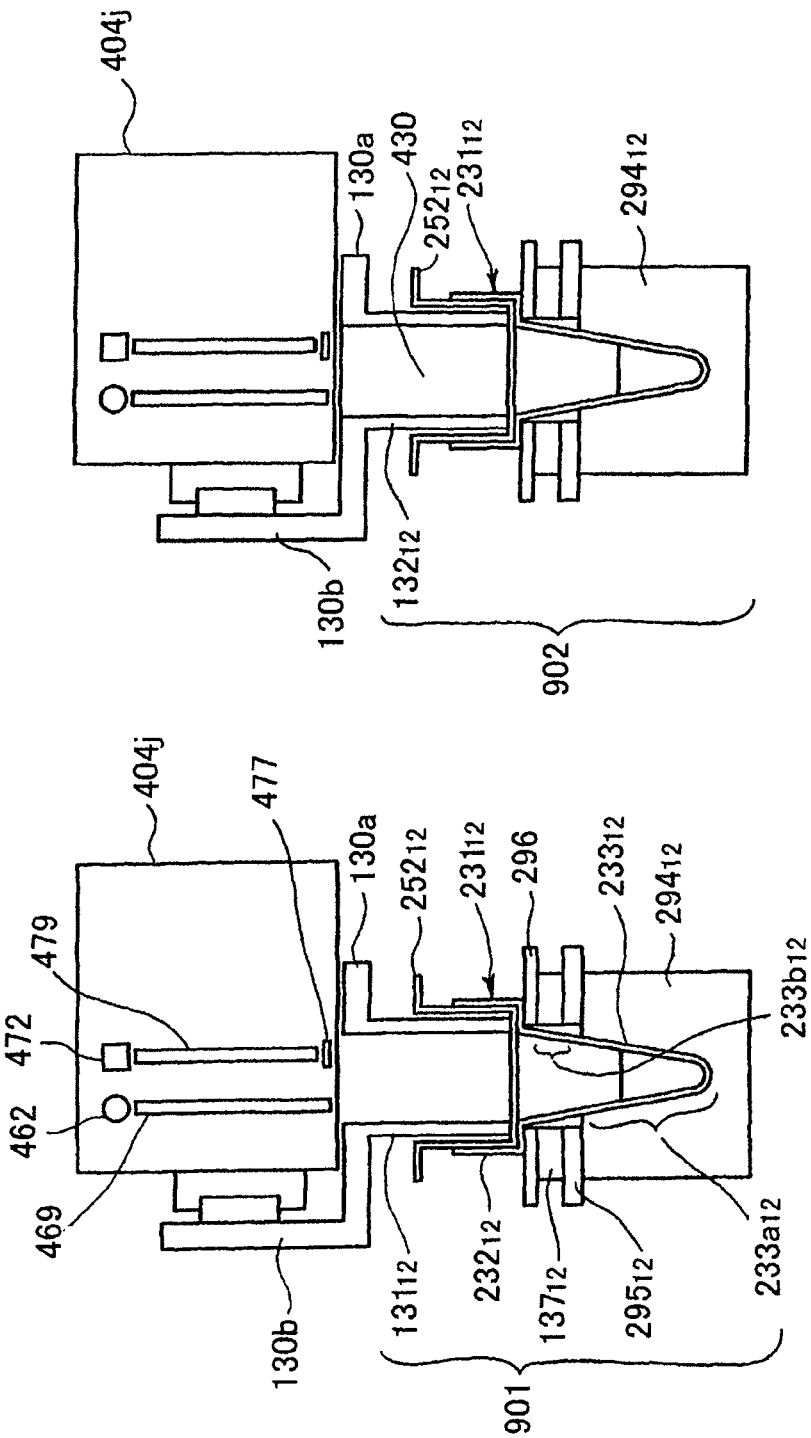

REACTION CONTAINER CONTROL SYSTEM

CROSS REFERENCE

This application is a division of U.S. patent application Ser. No. 13/983,508, which is a 371 national phase of international patent application number PCT/JP2012/052632, filed Feb. 6, 2012, which claims priority to Japanese patent application number 2011-023378, filed Feb. 4, 2011, the entire disclosures of which are hereby incorporated herein by reference.

TECHNICAL FIELD

The present invention relates to an automatic response/light measurement device and a method therefor.

BACKGROUND ART

At the time reactions such as amplification of nucleic acids (DNA, RNA, and the like) and the fragments thereof (oligonucleotides, nucleotides, and the like) are performed, in tests that require quantitativeness, such as the analysis of gene expression levels, it becomes necessary to perform the amplification such that the ratio of the relative amounts of the respective nucleic acids can be known. Consequently, by using the real-time PCR method, and by using a device provided with a thermal cycler and a fluorescence spectrophotometer, analysis by electrophoresis is made unnecessary as a result of the generation process of the DNA amplification products in PCR being detected and analyzed in real time. Furthermore, as a DNA amplification method that performs amplification while maintaining the quantitativeness with respect to the ratio of the relative amounts of the DNA or RNA contained in the sample before amplification, the SPIA (Single Primer Isothermal Amplification) method is used. In the SPIA method, the linear DNA amplification method resulting from an isothermal reaction utilizing DNA/RNA chimera primer, DNA polymerase, and RNaseH has become used.

In a case where processing such as nucleic acid amplification, and measurements thereof are performed, conventionally, the target compound is separated and extracted from the sample by using a filter by means of a manual method, by using magnetic particles and adsorption on an inner wall of a container or a pipette tip by means of a magnetic field, or by using a centrifuge. The separated and extracted target compound is transferred and introduced into a reaction container together with a reaction solution by a manual method and the like, and upon sealing of the reaction container using a manual method and the like, at the time reactions are performed using a temperature control device for reactions, optical measurements are performed with respect to the reaction container using a light measuring device (Patent Document 1).

In a case where the processing is executed by a manual method, a large burden is forced on the user. Furthermore, in a case where the processing is executed by combining a dispenser, a centrifuge, a magnetic force device, a temperature controller, a device for sealing the reaction container, a light measurement device, and the like, there is a concern of the scale of the utilized devices increasing and of the work area expanding. In particular, in a case where a plurality of samples is handled, since it becomes necessary to separate and extract a plurality of target nucleic acids and for amplification to be to respectively performed, the labor thereof becomes even greater, and furthermore, there is a concern of the work area also expanding further.

Specifically, in a case where reactions of the nucleic acids (DNA, RNA, and the like) to be amplified, and the like, are performed within a plurality of reaction containers and these reactions are monitored by optical measurements, the measurements are performed by successively moving a single measuring device to the respective reaction containers by a manual method, or the measurements are performed by providing a measuring device to each of the respective reaction containers beforehand.

In the former case where a single measuring device is used, when the measuring device is attempted to be manually moved to the apertures of the reaction containers, there is a concern of subtle differences occurring in the measurement conditions for each reaction container as a result of subtle displacements or relative motions between the reaction container and the measuring device.

In the latter case where a measuring device is provided to each of the respective reaction containers, although the positioning accuracy becomes high, there is a concern of the device scale expanding, and of the manufacturing costs increasing. Furthermore, although it is preferable to seal the apertures of the reaction containers at the time of temperature control and the measurements, it is time-consuming to perform sealing, or opening and closing, with respect to a plurality of reaction containers by a manual method with a lid, and in particular, there is a concern of the lid becoming adhered to the container apertures such that it becomes difficult to easily open the lid, and of contamination occurring from the liquid attached to the inside of the lid dripping or splashing. Furthermore, there is a concern of providing a dedicated opening and closing mechanism of the lid complicating the device, and increasing the manufacturing costs (Patent Document 2).

Moreover, at the time an optical measurement is performed on a sealed reaction container, there is a concern of the lid which has transparency, or the optical elements, becoming cloudy from condensation, and the measurements becoming difficult.

Consequently, in order to perform nucleic acid amplification and the like, as a precondition thereof, specialized researchers or technicians become necessary, and this situation is preventing the generalization of genetic analysis and the expansion of clinical applications in hospitals, and the like.

Therefore, at the time of clinical use and the like, in order to prevent cross-contamination and to reduce user labor, and to easily perform from the extraction, the amplification, and further, by means of a measurement, the genetic analysis of nucleic acids, then the automation of steps from the extraction of the target compound, reactions such as amplification, up to the measurements, the miniaturization of the device, and the provision of an inexpensive, high-accuracy device are important.

PRIOR ART DOCUMENTS

[Patent Document 1] International Publication WO96/29602

[Patent Document 2] Japanese Unexamined Patent Publication No. 2002-10777

SUMMARY OF THE INVENTION

Problems to be Solved by the Invention

Therefore, the present invention is one that has been achieved in order to solve the problems mentioned above. A first object thereof is in providing an automatic response/ light measurement device and an automatic response/light measurement method that automates optical measurements with respect to reactions of nucleic acids and the like, reduces user labor, performs processing rapidly and efficiently, and which also can be inexpensively manufactured and utilized without expanding the scale of the device or complicating the device.

A second object thereof is in providing an automatic response/light measurement device and an automatic response/light measurement method in which optical measurements with a high accuracy with respect to the solutions within the reaction containers, in which reactions such as amplification of nucleic acids are performed, are possible.

A third object thereof is in providing an automatic response/light measurement device and an automatic response/light measurement method that, by consistently automating the optical measurements with respect to the reaction containers, in which reactions such as amplification of nucleic acids are performed, and the associated processing therein, processing with a high reliability can be performed by preventing with certainty contaminations due to the entry of contaminants into the reaction containers from the exterior, or fluid leakage from the reaction containers for example.

Means for Solving the Problem

A first aspect of the invention is an automatic response/ light measurement device comprising: a container group in which two or more reaction containers are arranged; a measurement mount provided with two or more coupling ends that are directly or indirectly joinable with apertures of the reaction containers, and have light guide portions that optically connect with the interior of the joined reaction containers; a mount transfer mechanism that makes the mount relatively movable with respect to the container group; a measuring device provided on the mount and having a measuring end having at least one light guide portion that is optically connectable to the light guide portions of the coupling ends, that is able to receive light based on an optical state within the reaction containers via the measuring end; an on-mount measuring end transfer mechanism that makes the measuring end movable on the mount; and a measurement control portion that, following control of the mount transfer mechanism such that the coupling ends are simultaneously directly or indirectly joined with the apertures of the two or more reaction containers, controls the on-mount measuring end transfer mechanism such that the light guide portions of the coupling ends and the light guide portion of the measuring end are successively optically connected, and instructs a measurement by the measuring device.

It is preferable for the container group to have in addition to the reaction containers, two or more liquid housing parts that house liquids such as samples, reagents, and the like. Furthermore, the container group includes a microplate in which wells representing a plurality of liquid housing parts are arranged in a matrix form or a column (row) form, or a cartridge form container in which wells representing a plurality of liquid housing parts are arranged in a row form. In a case where amplification of nucleic acids is performed, the container group is provided with two or more liquid housing parts housing for example; a sample, a magnetic particle suspension in which magnetic particles that are able to capture the nucleic acids or the fragments thereof, which represent the amplification subject, are suspended, a solution for separating and extracting used for the separation and the extraction of the amplification subject, and an amplification solution used in nucleic acid amplification.

Here, the "amplification solution" represents, in a case where amplification is performed by the PCR method for example, a template DNA solution which is the amplification subject, a primer solution, a DNA polymerase solution, a nucleotide solution, a reaction buffer solution, and the like. In a case where amplification is performed by the SPIA method, it represents a DNA/RNA chimera primer solution, a DNA polymerase solution, an RNaseH solution, and the like. Furthermore, generally, methods for performing real-time PCR using fluorescent reagents containing a fluorescent compound include the intercalation method, the hybridization method, and the LUX method. In the "intercalation method", a fluorescent compound such as SYBR (registered trademark) GREEN I or ethidium bromide, enters into double-stranded DNA at the time of the elongation reaction, and is a method in which the DNA amount is measured by irradiating an excitation light and utilizing the fluorescent light-emitting characteristics. Therefore, at the very least, the fluorescent material and a quencher that suppresses the light emission of the fluorescent material must be contained within the amplification solution. The "hybridization method" is a method that detects only a target PCR product by using a DNA probe labeled with a fluorescent material in addition to a PCR primer. That is to say, as a result of the DNA probe labeled by fluorescent material hybridizing with the target PCR product, the hybridized DNA (amount) thereof is detected. The "LUX method" is one that utilizes a property in which the fluorescent light signal of the fluorescent compound labeling the oligonucleotide is affected by the shape (such as a sequence, a single-strand, or a double-strand) of the oligonucleotide thereof. In actual real-time PCR, a PCR primer (LUX primer) that is labeled with one type of a fluorescent compound and a contrastingly unlabeled PCR primer are used to perform real-time PCR. The LUX primer thereof is labeled with a fluorescent compound in the vicinity of the 3'-terminus, and is designed such that it takes a hairpin structure in the interval between the 5'-terminus. When the LUX primer takes a hairpin structure, the quenching effect is resolved, and the fluorescent light signal becomes increased. By measuring this signal increase, the amount of the PCR product can be measured.

Examples of the material of the containers, which includes the reaction containers, the lid, and the like, include resins such as polyethylene, polypropylene, polystyrene and acrylic, glass, metals, and metal compounds. The size of the containers is, in addition to several µL to several 100 µL of liquid being storable, a size in which the ends of the dispensing tips are insertable for example. In the case of a cylindrical shape, the diameter of the size of one container is several mm to several 10 mm, and the depth is several mm to several 10 mm for example.

It is preferable for the interior of the reaction containers to be temperature controllable by a temperature controller.

The "temperature controller" has a temperature source that is able to lower the temperature within the reaction containers, which house the liquids that become subjected to temperature control, based on a signal from the exterior for example. The temperature source is one in which, for example, a Peltier element, a heater, a cooling device, and the like is provided on a block-shaped member. In order to perform processing such as PCR, the temperature controller is preferably a thermal cycler using a Peltier element. It is preferable for temperature control to be achieved by a temperature controller provided to the container group or the stage, in which a temperature source, which has a Peltier element and the like, makes contact with or is adjacent to a portion or the entirety of the reaction container.

"Temperature control" represents, with respect to a liquid or a container that becomes the subject thereof, the maintaining of one or two or more set predetermined temperatures for set time periods, according to a specified sequence, and the execution at a specified frequency. The instructions to the temperature controller are carried out by sending a corresponding signal based on a program. An example of temperature control includes temperature control by the LAMP method using isothermal amplification, which is also possible.

The "predetermined temperature" is a target temperature that an object, such as a liquid that becomes the subject, is to reach. In a case where nucleic acids, such as the DNA contained in a liquid, or oligonucleotides and the like, which represent fragments of nucleic acids, are amplified by the PCR method for example, the predetermined temperature that is set is a temperature cycle performed in the PCR method. That is to say, it represents temperatures that are respectively necessary for the denaturation, the annealing or the hybridization, and the elongation of DNA of approximately 94° C., a temperature in the interval from 50° C. to 60° C., and a temperature of approximately 72° C. for example. On the other hand, in the case of the isothermal SPIA method, it becomes set at a fixed temperature, such as 55° C. for example.

Furthermore, the predetermined temperature includes a temperature for transition acceleration that shortens the transition time and keeps the single cycle time within a predetermined cycle time as a result of, in the case of a transition from a high-temperature predetermined temperature to a low-temperature predetermined temperature, performing cooling at a temperature for transition acceleration that is lower than these predetermined temperatures by means of the temperature controller, or, at the time of a transition from a low-temperature predetermined temperature to a high-temperature predetermined temperature, by performing heating at a temperature for transition acceleration that is even higher than these predetermined temperatures for example. The "predetermined time" is the time necessary for maintaining the respective temperatures, and although it depends on the type of the amplification method, the reagents and the amount of liquid used in the PCR method, and the shape, the material, the size, the thickness, and the like, of the nozzles, a single cycle is, in total, from several seconds to several 10 seconds for example, and the processing time for the PCR method as a whole is of the order of approximately several minutes to several 10 minutes for example. The transition time is also included in the predetermined time.

Examples of the "mount transfer mechanism" include mechanisms whereby the intervals between the reaction containers, that is to say, between the stage on which the reaction containers are provided and the measurement mount are relatively adjustable in the vertical direction of the measurement mount and within the horizontal plane for example. Examples of the movement within the horizontal plane include an XY axis transfer mechanism that performs movement of the stage or the measurement mount along the X axis and the Y axis, or a Y (X) axis transfer mechanism that performs movement along the Y axis or the X axis only. Examples of the movement of the measurement mount in the axial direction include a vertical transfer mechanism that moves the measurement mount in the Z axis direction thereof. This is determined based on the arrangement of the coupling ends provided to the measurement mount or the shape of the stage.

Here, the "measurement control portion" comprises a computer (CPU) built into the automatic response/light measurement device, and a program that drives the computer. Measurement control is achieved by transmitting signals through a DA converter to the respective control parts that drive the transfer mechanism for example.

The "coupling end" is directly joinable to the aperture of the reaction container, or indirectly joinable via the sealing lid and the like, and is one also having a light guide portion that is able to guide the light based on the optical state within the reaction container. The coupling end is a plate-shaped section of the measurement mount, and the light guide portion represents a hole piercingly provided in the plate-shaped section thereof, a transparent section, or an optical element such as a lens for example. In that case, the coupling end is directly or indirectly joined by adhesion to the aperture of the reaction container, or by directly fitting with the outer periphery of the aperture of the reaction container or by indirectly fitting via the sealing lid and the like. Alternatively, the coupling end represents a member of a cylindrical shape and the like that is provided such that it downwardly protrudes from the measurement mount, and is directly joined by being inserted into the interior of the reaction container or indirectly joined via the sealing lid, and the light guide portion is one provided with a transparent section, such as a cavity provided to the member of a cylindrical shape and the like, or an optical fiber, or an optical element, such as a lens. There is a case where the light guide portion comprises separate light guide portions for irradiation and receiving light. In a case where the coupling end is directly joined to the reaction container, it is preferable to form the reaction container such that it is sealable.

The "light guide portions of the coupling ends and the light guide portion of the measuring end are successively optically connected" represents that the light guide portions that penetrate the coupling ends and the light guide portion of the measuring end of the measuring device are optically connected by becoming opposed at a close proximity. Since the amount of light received by the measuring device at the moment of connection corresponds to a maximum value, the measurement control portion specifies the data to be measured by calculating the maximum value of the amount of light.

The "measuring device" is one that makes fluorescence and chemiluminescence measurements possible for example, and in the former case, it has a filter for the irradiation of one or two or more types of excitation light and the receiving of fluorescent light having one or two or more types of wavelengths. In addition, it is preferable for these to be guided using an optical fiber. The "measuring end" has, at the very least, an inlet for the light to be received provided in the measuring device, and in a case of a fluorescence measurement, has an outlet for the light to be irradiated.

The "on-mount measuring end transfer mechanism" is a mechanism that optically successively connects the light guide portions of the coupling ends and the light guide portion of the measuring end by continuously or intermittently moving the measuring end on the mount along the movement path passed by the coupling ends. There is a case where the measuring end and the measuring device body are integrally formed, and a case where the measuring end and the measuring device body are connected by a flexible light guide path, such as an optical fiber. In the former case, the on-mount measuring end transfer mechanism moves the measuring device as a whole, including the measuring end. In the latter case, only the measuring end is moved, and the measuring device as a whole is immobile for example.

It is necessary for the movement of the measuring end by the on-mount measuring end transfer mechanism to be performed such that the receiving of the light from all of the reaction containers to be measured is completed within the stable light receivable time. Here, the "stable light receivable time" represents the time in which the optical state within the reaction containers, for which the light is receivable, is stably maintained. In the case of the intercalation method or the LUX method of real-time PCR, or the TaqMan probe of the hybridization method for example, it corresponds to the time in which the elongation reaction of the respective cycles of PCR is performed. In a case where a FRET probe is used in the hybridization method, it corresponds to the time in which annealing is performed.

If the time taken for a single cycle is made several 10 seconds or several minutes for example, the stable light receivable time becomes several seconds. However, the fluorescent light detection amount of the initial cycles of a PCR reaction is below the detection limit, and the later cycles of the PCR reaction become a plateau state, and in order to secure quantitativeness by a strict definition, it must be within a range of the amplification curve in which an exponential PCR amplification can be observed. The present invention is one in which the stable light receivable time utilizes the fact that the movement time of the measuring end between the reaction containers can be used, and by performing the movement of the measuring end necessary for receiving the light from the respective reaction containers within the stable light receivable time, the receiving of the light from the plurality of reaction containers can be performed approximately in parallel by means of a single measuring device, or a sufficiently small number in comparison to the number of reaction containers, without using a complicated optical system and without expanding the scale of the device.

Since it is "a measuring end having at least one light guide portion", the measuring end can be made to have two light guide portions that are respectively connectable to the two light guide portions of the coupling ends aligned in a direction perpendicular to the movement direction of the measuring end, and be used as a single measuring device by switchingly guiding the light for example.

The "optical state" represents a state such as light emissions, colors, color changes, or light variations. The light based on the optical state represents light from light emissions or light variations, or reflected light from light irradiated with respect to colors or color changes, or transmitted light, scattered light and the like.

A second aspect of the invention is an automatic response/light measurement device, wherein the measuring device has a plurality of types of specific wavelength measuring devices capable of receiving light of specific wavelengths or specific wavelength bands, each of which has a measuring end having at least one light guide portion that is optically connected to said light guide portion of the coupling ends, and a measuring end bundling portion that bundles in parallel the plurality of measuring ends, and the measuring ends are movable in parallel on the mount by means of the on-mount measuring end transfer mechanism, and the measurement control portion, by means of the movement of the measuring ends, controls the on-mount measuring end transfer mechanism such that the light guide portions of the coupling ends and the light guide portions of the measuring ends of the specific wavelength measuring devices are successively optically connected.

Here, in a case where fluorescent light is measured, it is necessary to provide the measuring device or the specific wavelength measuring devices with an excitation light irradiation portion that irradiates a corresponding excitation light in addition to the light receiving portion. The measuring ends of the measuring device, which are optically connectable to the light guide portions of the coupling ends, are provided with a cavity, an optical element such as a lens, or a light guide path such as an optical fiber for example.

The "joining" is integrally or linkingly performed. "Integrally" represents joining such that the intervals between the measuring ends are mutually fixed and do not have any degrees of freedom. "Linkingly" represents joining such that the intervals between the measuring ends have degrees of freedom to some extent, such as in a chain. Furthermore, "in parallel" refers to a state in which the coupling ends are aligned in the order of joining along the same movement path that is set on the mount or on the container group.

According to the present aspect of the invention, by using a plurality of types of luminescent compounds, colored compounds, color changing compounds, or light variation compounds and performing amplification processing in parallel under the same conditions on a plurality of types of amplification subjects in a single reaction container, it is possible to perform multiplex PCR amplification or multiplex real-time PCR on a plurality of types of amplification subjects by using a primer labeled with a plurality of types of luminescent compounds for example.

Since it is "light of a specific wavelength or a specific wavelength band", it represents, in terms of visible light, a range of wavelengths such as a red light, a yellow light, a green light, a blue light or a violet light for example.

A third aspect of the invention is an automatic response/light measurement device, wherein the container group has sealing lids which have transparency, that are mounted on the apertures of the reaction containers and seal the reaction containers, the sealing lids are joinable with the coupling ends, and the measurement control portion controls the mount transfer mechanism such that the mount is moved so that the sealing lids are mounted on the coupling ends, and the coupling ends are indirectly joined with the apertures of the reaction containers via the sealing lids.

Here, the "sealing lid" includes, in addition to those that are inflexible and a plate form or block form, those that are a film form or a membrane form and have a flexibility. The "mounting" includes fitting, threading, friction, adsorption, attachment, adhesion, and the like. In these cases, detachable mounting is preferable.

A fourth aspect of the invention is an automatic response/light measurement device, wherein the mount transfer mechanism makes the mount relatively movable in a vertical direction with respect to the container group, and the measurement control portion, after controlling the mount transfer mechanism to indirectly join the coupling ends via the sealing lids such that they cover the apertures of the reaction containers, performs control such that it presses or shakes the sealing lids covering the apertures.

It is preferable for the coupling ends to be provided such that they downwardly protrude from the mount. In this case, the coupling ends, for example, have a shape such as a rod shape, a cylinder shape, a cone shape, and the like, and the lower end portions of the members are able to make contact with the sealing lids. The pressing or the shaking is performed by the transfer mechanism that moves the mount, which is linked with the coupling ends, along the Z axis for example.

A fifth aspect of the invention is an automatic response/ light measurement device having a heating portion that is able to heat the coupling ends.

Here, the heating of the coupling ends by the heating portion is performed for preventing direct or indirect condensation on the coupling ends at the time of temperature control of the reaction containers, which are directly or indirectly sealed by the coupling ends. The measurement control portion or the nucleic acid processing controller, following controlling the mount transfer mechanism such that the coupling ends are simultaneously directly or indirectly joined with the apertures of the two or more reaction containers, controls the heating portion such that direct or indirect condensation on the coupling ends is prevented. "Preventing direct or indirect condensation on the coupling ends" represents prevention of condensation on the end portions of the coupling ends themselves, and "preventing indirect condensation" represents preventing condensation on the sealing lids mounted on the coupling ends. Here, the "heating portion" is sufficient if it has a heating function at a temperature that is set based on the magnitude of an applied electric current or by an ON/OFF control.

A sixth aspect of the invention is an automatic response/ light measurement device having; a temperature controller that performs temperature control of the interior of the reaction containers by having a temperature source provided such that, with respect to the reaction containers having a lower side wall section and an upper side wall sections positioned further on the upper side than the lower side wall section, it is able to make contact with or approach the lower side wall sections, and a heating portion provided such that it is able to make contact with or approach the upper side wall sections, and that has a heat source that is able to heat the upper side wall sections.

Here, the "lower side wall section" represents a wall section or a portion thereof including the bottom portion that encloses a volume section, which is a portion (1% to 90% for example) of the entire volume of the reaction container in which a predetermined rated liquid amount is housed. The lower side wall section represents a section of the wall section from the liquid surface of the housed rated volume of liquid to the bottom portion for example. In a case where the reaction containers comprise a wide-mouthed piping part, to which the coupling ends are mounted, and a narrow-mouthed piping part, it is provided on the narrow-mouthed piping part. The "upper side wall section" represents, within the entire volume of the reaction container, a container section enclosing the remaining volume of the lower side container section, in which the rated liquid amount is housed, or a portion thereof. The "upper side wall section" is normally preferably provided leaving a spacing with the lower side wall section, and on the upper side in the vertical direction. The upper side wall section is closer to the aperture than the lower side wall section, although it is provided on the lower side of the section on which the coupling end is mounted. In the case of the container comprising the wide-mouthed piping part and the narrow-mouthed piping part, it is provided on the narrow-mouthed piping part for example. The upper side wall section is preferably provided as a band shape along the circumference of the container wall for example.

The measurement control portion, following controlling the mount transfer mechanism such that the coupling ends are simultaneously directly or indirectly joined with the apertures of the reaction containers, controls the heating portion such that direct or indirect condensation on the coupling ends is prevented. "Indirectly joined" represents a case where the coupling ends are joined with the reaction containers via the sealing lids. "Control of the heating portion" is performed according to the "temperature control" for preventing condensation. The heating temperature is set to a temperature among temperatures (a temperature necessary for preventing condensation that exceeds the dew point temperature of water vapor but is a temperature that is sufficiently lower than the melting point of the raw material of the reaction container. These are determined by the volume, the shape or the raw material of the reaction container, the pressure or the humidity within the reaction container, the content of the temperature control including the predetermined temperature, the liquid amount, the composition of the solution, the temperature, the pressure, the processing aims and the like) that are from several degrees to several ten degrees higher than the respective predetermined temperatures set by the temperature control for example. It is controlled such that it is set from 1° C. to 60° C., or preferably of the order of approximately 5° C. higher than the predetermined temperature for example. In a case where the amplification is by PCR for example, heating is performed in a constant temperature state at the maximum predetermined temperature, namely a temperature several degrees higher than 94° C., such as 100° C. Alternatively, heating is performed such that it follows temperatures that are several degrees higher than the respective predetermined temperatures corresponding to the temperature control. Furthermore, in an isothermal case, in a case where the predetermined temperature is approximately 55° C., heating is performed at a temperature that is several degrees higher for example, namely from 60° C. to 70° C.

As a result of the heating portion performing heating with respect to the reaction containers rather than the coupling ends, thermal effects toward the optical system elements provided to the coupling ends or the measuring ends in the proximity of the coupling ends are reduced, and the degradation of the optical system elements such as prisms, optical fibers, various lenses such as rod lenses, mirrors, and waveguide tubes, can be prevented, or the reliability of the images obtained via the optical system elements can be increased.

A seventh aspect of the invention is an automatic response/light measurement device, wherein the measurement mount is provided to a nozzle head having a suction-discharge mechanism that performs suction and discharge of gases, and one or two or more nozzles that detachably mount dispensing tips in which the suction and the discharge of liquids is possible by means of the suction-discharge mechanism, and the mount transfer mechanism has a nozzle head transfer mechanism that makes the nozzle head relatively movable between the container groups.

In this case, in addition to further providing a magnetic force part that is able to apply or remove a magnetic force within the dispensing tips mounted on the nozzles or liquid housing parts provided in the container group, and which is able to adsorb the magnetic particles on an inner wall of the dispensing tips or the liquid housing parts, it is preferable to provide an extraction control part that controls the suction-discharge mechanism, the transfer mechanism, and the magnetic force part, and as the reaction solution, separates and extracts the solution of the amplification subject from the sample and houses it within the liquid housing parts as a portion of the amplification solution.

Here, the "solution for separating and extracting" includes a dissolving solution that breaks down or dissolves the protein forming the cell walls and the like contained in the sample and discharges the nucleic acids or the fragments thereof to the outside of the bacteria or the cell, a buffer solution that simplifies the capture of the nucleic acids or the fragments thereof by the magnetic particles, and additionally, a solution that dissociates from the magnetic particles, the nucleic acids or the fragments of nucleic acids captured by the magnetic particles. In order to perform the separation of the nucleic acids or the fragments thereof, it is preferable to repeat the suction and the discharge of the mixed solution.

The "dispensing tip" comprises for example a thick diameter portion, a narrow diameter portion, and a transition portion that communicates between the thick diameter portion and the narrow diameter portion. The thick diameter portion has an aperture for mounting, into which the lower end of the nozzle is inserted and the nozzle is mounted, and the narrow diameter portion has an end mouth portion in which liquids can flow in and flow out by means of the suction and discharge of gases by the suction-discharge mechanism. The dispensing tip and the nozzle are manufactured from organic substances such as resins of polypropylene, polystyrene, polyester, acrylic, and the like, and inorganic substances such as glass, ceramics, metals including stainless steel, metal compounds, and semiconductors.

The "suction-discharge mechanism" is for example a mechanism formed by a cylinder, a piston that slides within the cylinder, a nut portion joined to the piston, a ball screw on which the nut portion is threaded, and a motor that rotatingly drives the ball screw in both forward and reverse directions.

In a case where two or more nozzles are used, by respectively arranging two or more container groups so as to correspond to the respective nozzles within two or more exclusive regions corresponding to the respective nozzles, in which a single nozzle enters and the other nozzles do not enter, and by setting the respective exclusive regions for each different sample, cross-contamination between samples can be prevented with certainty.

An eighth aspect of the invention is an automatic response/light measurement device, wherein the container group comprises two or more exclusive regions corresponding to the nozzles of the respective groups, which comprise one or two or more nozzles, in which nozzles of a single group enter and the nozzles of other groups do not enter, and the respective exclusive regions at the very least have at least one reaction container, one or two or more liquid housing parts that house reaction solutions used in the reactions, and sealing lids that are transportable to the reaction containers using the coupling ends and are able to seal the reaction solutions housed in the reaction containers, and the mount is extendingly provided across all of the exclusive regions such that the coupling ends of the measurement mount are associated such that coupling ends of a single group, which comprises one or two or more coupling ends, enter the respective exclusive regions and the coupling ends of other groups do not enter.

In order to make "the nozzles of a single group enter and the nozzles of the other groups not enter" or "the coupling ends of a single group enter and the coupling ends of the other groups not enter", for example, this is performed by providing an exclusive region control part that controls the nozzle head transfer mechanism such that nozzles of a single group enter the respective exclusive regions and the nozzles of the other groups do not enter, and controls the measuring device transfer mechanism such that the coupling ends of a single group enter the respective exclusive regions and the coupling ends of the other groups do not enter.

A ninth aspect of the invention is an automatic response/light measurement device comprising: a nozzle head provided with a suction-discharge mechanism that performs suction and discharge of gases, and one or two or more nozzles that detachably mount dispensing tips in which the suction and the discharge of liquids is possible by means of the suction-discharge mechanism; a container group having at the very least one or two or more liquid housing parts that house reaction solutions used for various reactions, a liquid housing part that houses a magnetic particle suspension in which magnetic particles that are able to capture a target compound are suspended, a liquid housing part that houses a sample, one or two or more liquid housing parts that house a solution for separating and extracting of the target compound, and two or more reaction containers; a nozzle head transfer mechanism that makes an interval between the nozzle head and the container group relatively movable; a magnetic force part that is able to adsorb the magnetic particles on an inner wall of the dispensing tips mounted on the nozzles; a measurement mount provided to the nozzle head, and provided with two or more coupling ends that are directly or indirectly joinable with the apertures of the reaction containers, and have light guide portions that optically connect with the interior of the joined reaction containers; a measuring device provided on the mount, that has measuring ends having light guide portions that optically connect with the light guide portions of the coupling ends, and is able to receive light based on an optical state within the reaction container via the measuring ends; an on-mount measuring end transfer mechanism that makes the measuring ends movable on the mount; and a magnetic force part that is able to apply or remove a magnetic force that is able to adsorb the magnetic particles on an inner wall of the dispensing tips mounted on the nozzles; and has a separation and extraction control that, at the very least, controls the suction-discharge mechanism, the nozzle head transfer mechanism, and the magnetic force part and controls the separation and the extraction of the target compound; and a measurement control portion that, at the very least, controls the suction-discharge mechanism and the nozzle head transfer mechanism, and following movement of the mount such that the coupling ends simultaneously directly or indirectly join with the apertures of the two or more reaction containers, and following control of the on-mount measuring end transfer mechanism and movement of the mount such that the coupling ends simultaneously directly or indirectly join with the apertures of the two or more reaction containers, controls the on-mount measuring end transfer mechanism such that the light guide portions of the coupling ends and light guide portions of the measuring ends are successively optically connected, and instructs a measurement by the measuring device.

Here, the "reaction solution" is for example an amplification solution used for nucleic acid amplification. Furthermore, the "target compound" represents nucleic acids or the fragments thereof, which is the amplification subject. It is preferable to provide a lid detaching mechanism that detaches the sealing lids from the coupling ends, or a tip detaching mechanism that detaches the dispensing tips from the nozzles. In the present device, it is preferable to provide a sample supplying device having a dispensing function that supplies the samples, the reagents, the washing liquids, the buffers, and the like that are necessary for the container group at a position separate to the stage of the automated reaction/light device, and to make the whole stage, to which the supplied container group is built-in, be automatically moved to the position of the stage of the automatic response/ light measurement device and to be made exchangeable. Consequently, processing, including preparation processing such as the dispensing processing or the supplying processing with respect to the container group, can be consistently performed.

A tenth aspect of the invention is an automatic response/light measurement device, wherein the measuring device has a plurality of types of specific wavelength devices capable of receiving light of specific wavelengths or specific wavelength bands, each of which has a measuring end having at least one light guide portion that is optically connected to said light guide portions of the coupling ends, and a measuring end bundling portion that bundles the interval between the plurality of measuring ends in parallel, and the measuring ends are movable in parallel on the mount by means of the on-mount measuring end transfer mechanism, and the measurement control portion controls the on-mount measuring end transfer mechanism such that, by means of the movement of the measuring ends, the light guide portions of the coupling ends and the light guide portions of the measuring ends of the specific wavelength measuring devices are successively optically connected.

An eleventh aspect of the invention is an automatic response/light measurement device, wherein the container group has sealing lids which have transparency and are able to seal the reaction containers by fitting with the apertures of the reaction containers, the sealing lids are mountable on the coupling ends, the measuring device is able to receive light based on an optical state within the reaction containers via the coupling ends and the sealing lids, and in addition, further has a sealing control part that controls the nozzle head transfer mechanism such that the sealing lids are simultaneously mounted on the coupling ends, and the measurement control portion, following control of the nozzle head transfer mechanism such that the coupling ends are simultaneously joined with the apertures of the reaction containers indirectly via the sealing lids, controls the on-mount measuring end transfer mechanism such that the light guide portions of the coupling ends and light guide portions of the measuring ends are successively optically connected.

A twelfth aspect of the invention is an automatic response/light measurement device further having a mount Z axis transfer mechanism that makes the measurement mount provided to the nozzle head movable in the vertical direction with respect to the nozzle head, and further having a pressing and the like control part that, following control of the mount Z axis transfer mechanism and indirectly joining the coupling ends with the apertures of the reaction containers, performs control such that the sealing lids covering the apertures are pressed or shaken. Here, the "mount Z axis transfer mechanism" is one provided separately to the "nozzle head transfer mechanism".

A thirteenth aspect of the invention is an automatic response/light measurement device having a heating portion that is able to heat the coupling ends.

Here, the heating portion, after the sealing lids are simultaneously mounted on the coupling ends and following control of the mount transfer mechanism such that the coupling ends are simultaneously indirectly joined with the apertures of the two or more reaction containers, is controlled by the measurement control portion or the nucleic acid processing controller such that it heats the sealing lids via the coupling ends.

A fourteenth aspect of the invention is an automatic response/light measurement device having: a temperature controller having a temperature source which is provided such that, with respect to the reaction container having a lower side wall section and an upper side wall section positioned further on the upper side of the lower side wall section, it is able to make contact with or approach the lower side wall sections, and that performs temperature control of the interior of the reaction containers; and a heating portion which is provided such that it is able to make contact with or approach the upper side wall sections, and that has a heat source that is able to heat the upper side wall sections.

The heating portion, following control of the mount transfer mechanism by means of the rated control part or the nucleic acid processing controller such that the coupling ends are simultaneously directly or indirectly joined with the apertures of the reaction containers, is controlled such that, at the time of temperature control by means of the temperature controller, direct or indirect condensation on the coupling ends is prevented.

A fifteenth aspect of the invention is an automatic response/light measurement device, wherein the container group comprises, two or more exclusive regions corresponding to the nozzles of the respective groups, which comprise one or two or more nozzles, in which nozzles of a single group enter and the nozzles of other groups do not enter, and the respective exclusive regions at the very least have at least one reaction container, one or two or more liquid housing parts that house reaction solutions used in the reactions, a liquid housing part that houses a magnetic particle suspension in which magnetic particles that are able to capture a target compound are suspended, a liquid housing part that houses a sample, two or more liquid housing parts that house a solution for separating and extracting of the target compound, and sealing lids that are transportable to the reaction containers using the coupling ends and are able to seal the reaction solutions housed in the reaction containers, the mount is extendingly provided across all of the exclusive regions such that the coupling ends of the measurement mount are such that the coupling ends of a single group which comprises one or two or more coupling ends, enter each of the respective exclusive regions, and the coupling ends of other groups do not enter, the nozzle head transfer mechanism is controlled such that the nozzles of a single group enter the respective exclusive regions and the nozzles of the other groups do not enter, and there is further provided an exclusive region control part that controls the on-mount measuring end transfer mechanism such that the coupling ends of a single group enter the respective exclusive regions and the coupling ends of the other groups do not enter.

A sixteenth aspect of the invention is an automatic response/light measurement method, that performs measurement by; moving a measurement mount to which two or more coupling ends having light guide portions are provided, with respect to apertures of two or more reaction containers arranged in a container group, directly or indirectly simultaneously joining the apertures of the reaction containers and the coupling ends, and optically connecting the interior of the joined reaction containers and the light guide portions provided to the coupling ends, performing temperature control within the reaction containers, moving the measuring ends provided to the measuring device on the mount, so that the light guide portions provided to the coupling ends and the light guide portions of the measuring ends are successively optically connected, and making the measuring device receive light based on an optical state within the reaction containers, via the measuring ends.

A seventeenth aspect of the invention is an automatic response/light measurement method, wherein a plurality of types of specific wavelength measuring devices that are able to receive light of specific wavelengths or specific wavelength bands at the time of the measurement are provided as the measuring device, and the light guide portions of measuring ends of the specific wavelength measuring devices are optically connected with the light guide portions of the coupling ends and are able to receive light of specific wavelengths or specific wavelength bands based on an optical state within the reaction containers via the measuring ends, and measurement is performed by bundling the measuring ends of the plurality of types of specific wavelength measuring devices and moving these on the mount in parallel, to thereby successively optically connected the light guide portions provided to the coupling ends and light guide portions of the measuring ends, and making the specific wavelength measuring devices receive light of specific wavelengths or specific wavelength bands based on the optical state within the reaction containers, via the measuring ends.

An eighteenth aspect of the invention is an automatic response/light measurement method that moves the mount with respect to two or more sealing lids which have transparency, that are arranged in the container group and are fittable with the apertures of the reaction containers, and moves the mount with respect to the apertures of the reaction containers following simultaneous mounting of the sealing lids on the coupling ends.

A nineteenth aspect of the invention is an automatic response/light measurement method that, following mounting of the reaction containers on the measurement mount, performs pressing or shaking with respect to the sealing lids covering the apertures of the reaction containers.

A twentieth aspect of the invention is an automatic response/light measurement method, that performs measurement by: detachably mounting dispensing tips on nozzles provided to nozzle heads, which perform suction and discharge of gases, separating a target compound using; a nozzle head transfer mechanism that relatively moves between a magnetic force part, the nozzle head, and a container group, a magnetic particle suspension in which magnetic particles that are able to capture the target compound housed in the container group are suspended, a sample, and a solution for separating and extracting of the target compound, introducing the separated target compound and a reaction solution used for a reaction into a plurality of reaction containers provided to the container group, moving at the very least by means of the nozzle head transfer mechanism, a measurement mount that, in addition to being provided to the nozzle head, is provided with two or more coupling ends having light guide portions, with respect to apertures of the reaction containers, directly or indirectly simultaneously joining the apertures of the reaction containers and the coupling ends, and optically connecting the interior of the joined reaction containers and the light guide portions provided to the coupling ends, performing temperature control within the reaction containers, moving the measuring ends provided to the measuring device on the mount, so that the light guide portions of the coupling ends and the light guide portions of the measuring ends are optically successively connected, and making the measuring device receive light based on an optical state within the reaction containers, via the measuring ends.

A twenty-first aspect of the invention is an automatic response/light measurement method, wherein at the time of directly or indirectly joining the apertures of the reaction containers and the coupling ends, and performing temperature control within the reaction containers, condensation on the coupling ends is directly or indirectly prevented by a heat source positioned further on an upper side than a lower side wall section of the reaction container and provided making contact with or approaching an upper side section of the reaction container, according to temperature control of a temperature source provided making contact with or approaching the lower side wall section.

A twenty-second aspect of the invention is an automatic response/light measurement device comprising: a container group in which two or more reaction containers are arranged; a plurality of types of specific wavelength measuring devices provided with measuring ends having light guide portions that are optically connectable with the interior of the reaction containers, and that are able to receive light of specific wavelengths or specific wavelength bands based on an optical state within the reaction containers via the measuring ends; a measuring end bundling portion that bundles the plurality of measuring ends in parallel; a measuring end transfer mechanism that makes the bundled measuring ends relatively movable with respect to the container group; and a measurement control portion that, by moving the measuring ends along a movement path that successively passes apertures of the reaction containers, controls the measuring end transfer mechanism such that light guide portions of the measuring ends and the interior of the reaction containers are successively optically connected, and, with respect to the specific wavelength measuring devices, instructs a measurement by receiving light of the specific wavelengths or specific wavelength bands based on an optical state within the reaction containers. Here, the "measuring end transfer mechanism" corresponds to the mount transfer mechanism and the on-mount measuring end transfer mechanism.

A twenty-third aspect of the invention is an automatic response/light measurement device further comprising a measurement mount provided with two or more coupling ends that are directly or indirectly joinable with the apertures of the reaction containers, and that have light guide portions that optically connect with the interior of the joined reaction containers, wherein the measuring ends of the specific wavelength measuring device are provided on the mount, and in addition, the measuring end transfer mechanism has a mount transfer mechanism that makes the mount relatively movable with respect to the container group, and an on-mount measuring end transfer mechanism that makes the measuring ends of the specific wavelength measuring device movable in parallel on the mount.

A twenty-fourth aspect of the invention is a reaction container control system comprising: a reaction container, a temperature controller that, with respect to the reaction container having a lower side wall section of the reaction container and an upper side wall section positioned on an upper side of the lower side wall section, has a temperature source provided such that it is able to make contact with or approach the lower side wall section, and that performs temperature control within the reaction container; and a heating portion that is provided such that it is able to make contact with or approach the upper side wall section, and that has a heat source that is able to heat the upper side wall section.

The heating portion is such that the heating portion is controlled so that the condensation on the member for light measurement mounted on the aperture of the reaction container is prevented. Here, the "member for light measurement" represents a member for measurement that measures the optical state within the reaction container, and includes; a sealing lid which has transparency and that is mounted on the aperture of the reaction container, the coupling end, the end portion of an optical fiber, a waveguide tube, various lenses such as a rod lens, a mirror, an optical system element such as a prism, or a member in which these are built-in.

A twenty-fifth aspect of the invention is a reaction container control system, wherein the reaction container comprises a wide-mouthed piping part, and a narrow-mouthed piping part that is formed narrower than the wide-mouthed piping part and is provided on a lower side of the wide-mouthed piping part and communicated with the wide-mouthed piping part, a member for light measurement is mountable on the wide-mouthed piping part, liquids are housable in the narrow-mouthed piping part, and the lower side wall section and the upper side wall section are provided to the narrow-mouthed piping part.

Effects of the Invention

According to the first aspect of the invention, the ninth aspect of the invention, the sixteenth aspect of the invention, the twentieth aspect of the invention or the twenty-third aspect of the invention, by joining the apertures of the plurality of reaction containers and the coupling ends provided to the measurement mount, the interval between the plurality of reaction containers and the measurement mount is integrated and the positional relationship is fixed, and the light guide portions provided to the coupling ends are smoothly optically connected with the reaction containers in a state in which subtle displacements or relative movements that occur at the time of positioning in a case where they are separated are excluded, and it is possible to guide the light of the optical state of the central sections of the reaction containers to the measuring device mounted on the measurement mount. Further, with respect to the plurality of reaction containers that are correctly positioned via the measurement mount, by moving the measuring device continuously or intermittently such that the measuring end of the measuring device set on the measuring mount passes a predetermined path, such as a linear path, that passes the end portions of the light guide portions on the mount, the light guide portions of the coupling ends and the light guide portions of the measuring ends of the measuring device are successively optically connected with certainty, and the measurement can be performed by receiving the light from the fixed position of the reaction container with a high accuracy. The measurement result and the amplification curve from real-time PCR are created, and can be utilized in various analyses, such as the determination of the initial concentration of DNA.

Furthermore, since the measurement of the plurality of reaction containers can be performed with a single measuring device by utilizing the stable light receivable time, the expansion of the scale of the device is suppressed, and the manufacturing costs can be reduced. Moreover, since it is possible to measure by successively moving the upper ends of the light guide portions of the coupling ends joined with the reaction containers, through the shortest distance along the predetermined path passed by the measuring ends, a light switching mechanism and the like is not necessary, and the measurements can be performed in parallel by a simple mechanism of only a transfer mechanism between the plurality of reaction containers.

Since the reactions and the measurements are performed by sealing the reaction containers by joining the apertures of the reaction containers with joined portions, automatic measurements with a high reliability in which cross-contaminations can be prevented with certainty can be performed.

According to the second aspect of the invention, the tenth aspect of the invention, the seventeenth aspect of the invention, the twenty-second aspect of the invention, or the twenty-third aspect of the invention, by using a plurality of types of luminescent compounds, colored compounds, color changing compounds, or light variation compounds, within a single reaction container, then for example in a case where amplification processing is performed in parallel under the same conditions on a plurality of types of amplification subjects, it is possible to perform multiplex PCR amplification or multiplex real-time PCR on a plurality of types of amplification subjects by using a primer labeled with a plurality of types of luminescent compounds and the like. At that time, by combining the switching of the receiving of the light of a plurality of types of specific wavelengths or specific wavelength bands from the plurality of types of luminescent compounds and the like, with a mechanism utilizing the stable light receivable time that is used at the time of movement between the plurality of reaction containers, it is not necessary to separately provide a special light switching mechanism, and the device mechanism can be simplified and manufacturing costs can be reduced. Furthermore, since the respective specific wavelength measuring devices each receive light of a specific wavelength or a specific wavelength band, the effects of other specific wavelengths or specific wavelength bands are not received, and high-accuracy measurements can be performed. Moreover, since the respective specific wavelength measuring devices are each modularized such that removal and addition can be performed, processing with a high versatility according to the processing aims can be performed. In the case of the second aspect of the invention, the tenth aspect of the invention, the seventeenth aspect of the invention, or the twenty-third aspect of the invention, since the measuring device is moved following joining of the apertures of the reaction containers with the coupling ends, and the integration of the reaction containers and the mount, the receiving of light can be performed with a high accuracy.

According to the third aspect of the invention, the eleventh aspect of the invention, or the eighteenth aspect of the invention, by mounting the sealing lids arranged in the container group on the coupling ends, it is possible to perform mounting to the apertures of the reaction containers by means of the movement of the measurement mount. Therefore the housed substances within the reaction containers do not make direct contact with the coupling ends of the mount, and hence cross-contaminations can be effectively prevented. Furthermore, since it is not necessary to provide a dedicated mechanism for mounting the sealing lid on the reaction containers, the scale of the device is not expanded, and the manufacturing costs are reduced.

According to the fourth aspect of the invention, the twelfth aspect of the invention, or the nineteenth aspect of the invention, the sealing of the reaction containers can be performed with certainty by controlling the sealing lids covering the apertures of the reaction container such that they are pressed. Furthermore, by shaking the sealing lids, the sealed state between the apertures of the reaction container and the sealing lids can be rapidly and easily removed and released. Therefore, a high processing efficiency and reliability can be obtained.

According to the fifth aspect of the invention, or the thirteenth aspect of the invention, by performing control such that the coupling ends are heated, condensation at the time of temperature control of the reaction containers that are directly or indirectly sealed by the coupling ends is prevented, and measurements via the coupling ends or the sealing lids which have transparency, can be performed with certainty and a high accuracy.

According to the sixth aspect of the invention, the fourteenth aspect of the invention, or the twenty-first aspect of the invention, by performing control of the heating of the coupling end making direct or indirect contact by means of the lower side wall sections of the reaction containers, and therefore the temperature control of lower side wall section, and in addition, the heating control of the upper side wall sections of the reaction containers, direct or indirect condensation on the coupling ends can be prevented. Then, the coupling ends are not directly heated, and since the heating is performed at the upper side wall sections of the reaction containers, the direct effects of heating toward the optical system elements provided to the coupling ends can be reduced. Consequently, in addition to reducing or removing image distortions and the like from the degradation or the change in properties of the optical system elements, by performing temperature control such that, according to the heating, the temperatures of the lower side wall sections are guided to the respective predetermined temperatures set using a coolable Peltier element and the like, measurements with a high reliability can be performed. Further, since various optical system elements can be provided to the coupling ends, precise measurements with a high versatility can be performed. Furthermore, since the prevention of direct or indirect condensation on the coupling ends is achieved by heating the wall sections of the reaction containers, it is not necessary to provide a heating portion directly above the containers, and the structure directly above the containers, and therefore the structure of the device as a whole is simplified, and it is possible to further approach the coupling ends possessing optical system elements, to the containers and to perform the optical measurements with certainty.

According to the seventh aspect of the invention to the ninth aspect of the invention, the fifteenth aspect of the invention, or the twentieth aspect of the invention, as a result of the measurement mount being built into the nozzle head to which the nozzles are provided, a transfer mechanism (at the very least the X axis and Y axis directions) between the reaction containers of the measuring device is not separately provided, and since it can be combined with the transfer mechanism of the nozzles, the expansion of the scale of the device can be prevented. Furthermore, since the transfer to the reaction container of the sample solution, the reagent solutions, and the reaction solutions, which are to be housed within the reaction container, and which represent the measurement subject, and the preparation, can be performed using the functions of the nozzles, steps from the processing to the measurement of the measurement subject can be consistently, efficiently, and rapidly performed.

According to the twenty-fourth aspect of the invention and the twenty-fifth aspect of the invention, by performing heating control of the upper side wall sections of the reaction containers in addition to the temperature control of the lower side wall sections of the reaction containers, direct or indirect condensation on the member for light measurement for performing optical measurements of the optical state within the reaction containers is prevented. Then, the member for light measurement is not directly heated and since heating control of the upper side wall sections of the reaction containers is performed, the effects of heating toward the optical system elements provided to the member for light measurement can be reduced. Consequently, in addition to reducing or removing image distortions and the like from the degradation or the change in properties of the optical system elements, by performing temperature control such that, according to the heating, the temperatures of the lower side wall sections are guided to the respective predetermined temperatures set using a coolable Peltier element and the like, measurements with a high reliability are performed, and precise measurements with a high versatility can be performed. Furthermore, since the prevention of direct or indirect condensation on the member for light measurement is achieved by heating the wall sections of the reaction containers, it is not necessary to provide a heating portion directly above the containers, and the structure directly above the containers, and therefore the structure of the container reaction system as a whole is simplified, and since it is possible to further approach the member for light measurement possessing optical system elements, to the containers, optical measurements can be performed with certainty.

BRIEF DESCRIPTION OF THE DRAWINGS

FIG. 14A is a cross-sectional view showing a reaction container control system according to a first exemplary embodiment of the second embodiment.

FIG. 14B is a cross-sectional view showing a reaction container control system according to a second exemplary embodiment of the second embodiment.

BEST MODE FOR CARRYING OUT THE INVENTION

Next, an embodiment of the present invention is described with reference to the drawings. This embodiment is not to be interpreted as limiting the present invention unless particularly specified. Furthermore, in the embodiments, the same objects are denoted by the same reference symbols, and the descriptions are omitted.

Figure 1:
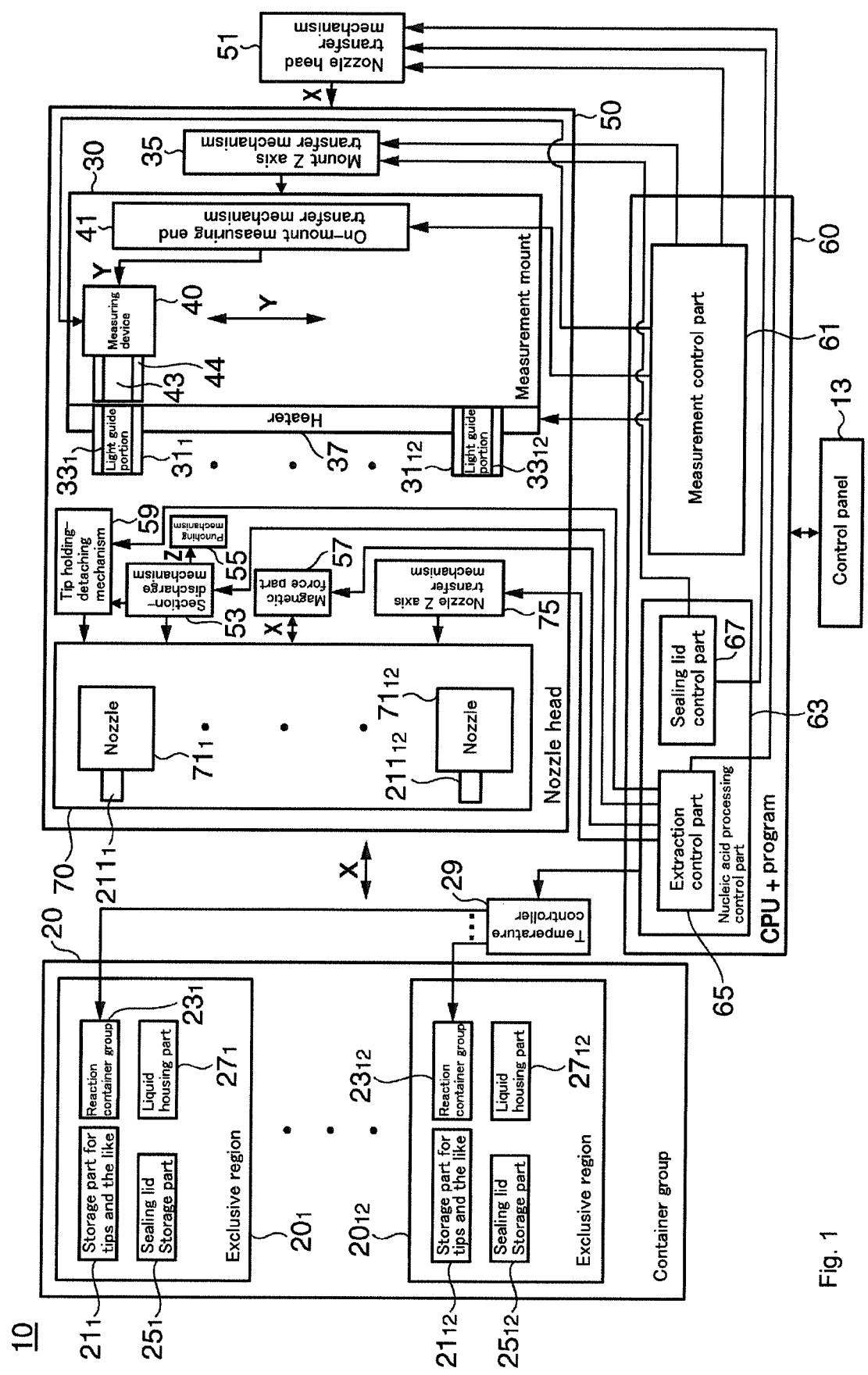
FIG. 1 is an overall block-diagram showing an automatic response/light measurement device according to a first embodiment of the present invention.

FIG. 1 shows a block-diagram of an automatic response/light measurement device 10 according to a first embodiment of the present invention.

The automatic response/light measurement device 10 broadly has: a plurality (twelve in this example) of container groups 20 in which reaction container groups $23_1$-$23_{12}$ are arranged; a nozzle head 50 that has a nozzle arrangement portion 70 in which a plurality (twelve in this example) of nozzles $71_1$-$71_{12}$ that detachably mount dispensing tips are arranged, and a measurement mount 30; a measuring device 40 provided on the mount 30; a nozzle head transfer mechanism 51 that makes the nozzle head 50 movable in the X axis direction for example; a temperature controller 29 that performs predetermined temperature control with respect to the reaction container groups $23_1$-$23_{12}$ of the container group; a CPU+program 60 composed of a CPU, a ROM, a RAM, various types of external memory, communication functions such as a LAN, and a program stored in the ROM, and the like; and a control panel 13 having a display portion such as a liquid crystal display, and an operation portion, such as operation keys or a touch panel.

The nozzle head 50 has: a mount Z axis transfer mechanism 35 that makes the mount 30 movable in the Z axis direction with respect to the container group 20 independent of the nozzle arrangement portion 70; a nozzle Z axis transfer mechanism 75 that makes the nozzle arrangement portion 70 movable in the Z axis direction with respect to the container group 20 independent of the mount 30; a magnetic force part 57 that, by means of a magnet 571 provided on narrow diameter portions $211_1a$ of dispensing tips $211_1$-$211_{12}$ detachably mounted on the nozzles $71_1$-$71_{12}$ such that they can approach and separate, is able to apply and remove a magnetic field with respect to the interior; a suction-discharge mechanism 53 that makes the suction and the discharge of liquids with respect to the dispensing tips $211_1$-$211_{12}$ mounted on the nozzles $71_1$-$71_{12}$ possible by performing the suction and the discharge of gases with respect to the nozzles $71_1$-$71_{12}$ and a punching mechanism 55 which is driven by the suction-discharge mechanism 53, for punching a film that covers the apertures of the liquid housing parts of the container group 20 to house various liquids in advance.

The mount 30 further has: an on-mount measuring end transfer mechanism 41 or 411 that moves a measuring end 44, and therefore the measuring device 40, along the Y axis direction, which is the longitudinal direction of the mount 30; a plurality (twelve in this example) of coupling ends $31_1$-$31_{12}$ that can be simultaneously directly or indirectly joined with the apertures of the reaction containers $23_{11}$-$23_{112}$ having light guide portions $33_1$-$33_{12}$ that optically connect with the interior of the joined reaction containers $23_{11}$-$23_{112}$; and a heater 37 as a heating portion that heats the coupling ends $31_1$-$31_{12}$ for preventing condensation at the ends of the coupling ends $31_1$-$31_{12}$ or on a mounted sealing lid 251 which has transparency. Furthermore, the measuring device 40 has the measuring end 44 to which is provided a light guide portion 43 optically connectable to the light guide portions $33_1$-$33_{12}$ which guide the movement of the measuring device 40 on the mount 30 along the Y axis direction and are provided on the coupling ends $31_1$-$31_{12}$ in the interior.

The container group 20 comprises a plurality (twelve in this example) of exclusive regions $20_1$-$20_{12}$ that correspond to the respective nozzles, in which a single (a single group corresponds to a single nozzle in this example) nozzle enters and the other nozzles do not enter. The exclusive regions $20_1$-$20_{12}$ have a liquid housing part groups $27_1$-$27_{12}$ which comprise a plurality of storage parts in which reagent solutions, and the like, are housed or are able to be housed, a sealing lid storage part $25_1$-$25_{12}$ in which one or two or more sealing lids 251 which have transparency, and that are detachably mounted on the coupling ends $31_1$-$31_{12}$ provided on the mount 30, are housed or are able to be housed, and housing parts for tips and the like $21_1$-$21_{12}$ that house a plurality of dispensing tips $211_1$-$211_{12}$ that are detachably mounted on the nozzle, samples, and the like. The liquid housing part group $27_1$-$27_{12}$ at the very least has one or two or more liquid housing parts that house a magnetic particle suspension, and two or more liquid housing parts that house a solution for separating and extracting used for the separation and the extraction of nucleic acids and the fragments thereof. Furthermore, if necessary, it additionally has two or more liquid housing parts that house an amplification solution used for the amplification of nucleic acids, and a liquid housing part that houses a sealing liquid for sealing the amplification solution housed in the reaction container $23_{11}$-$23_{112}$ within the reaction container $23_{11}$-$23_{112}$.

It is preferable for the exclusive regions $20_1$-$20_{12}$ to display identification data that identifies the respective exclusive regions $20_1$-$20_{12}$.

The CPU+program 60 at the very least has a nucleic acid processing controller 63 that performs instructions for a series of processes such as: the extraction and the amplification of nucleic acids and the fragments thereof, the sealing of the amplification solution, and the like, with respect to the temperature controller 29, the nozzle head transfer mechanism 51, the tip holding-detaching mechanism 59, the suction-discharge mechanism 53, the magnetic force part 57, and the nozzle Z axis transfer mechanism 75; and a measurement control portion 61 that, following control of the nozzle head transfer mechanism 51 and the mount Z axis transfer mechanism 35 such that the coupling ends $31_1$-$31_{12}$ are simultaneously directly or indirectly joined with the apertures of the plurality (twelve in this example) of reaction containers $231_1$-$231_{12}$, performs instructions for a measurement by the measuring device 40 by controlling the on-mount measuring end transfer mechanism 41 or 411 such that the light guide portions $33_1$-$33_{12}$ of the coupling ends $31_1$-$31_{12}$ and the light guide portion 43 of the measuring end 44 are optically connected.

Furthermore, the nucleic acid processing controller 63 has an extraction control part 65 and a sealing lid control part 67. The nucleic acid processing controller 63 has the extraction control part 65 that performs instructions for a series of processes for the extraction of nucleic acids and the fragments thereof with respect to the tip holding-detaching mechanism 59, the suction-discharge mechanism 53, the magnetic force part 57, the nozzle Z axis transfer mechanism 75, the nozzle head transfer mechanism 51, and the mount Z axis transfer mechanism 35, and the sealing lid control part 67 that performs instructions for the sealing process by the sealing lid with respect to the mount Z axis transfer mechanism 35 and the nozzle head transfer mechanism 51.

Figure 2:
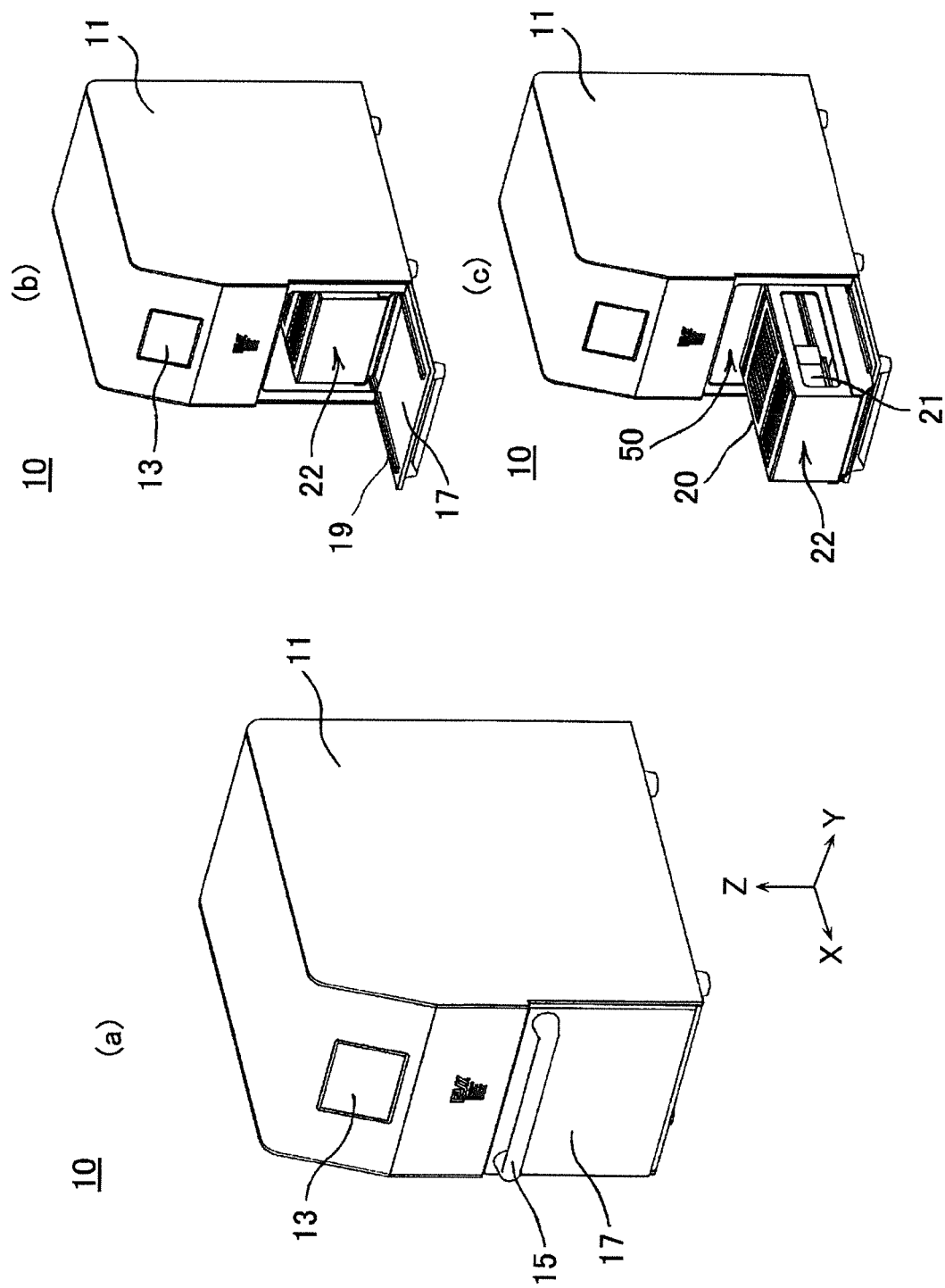
FIG. 2 is a perspective view showing a first exemplary embodiment of the automatic response/light measurement device shown in FIG. 1.

Herein, a variety of more specific exemplary embodiments of the automatic response/light measurement device 10 according to the embodiment of the present invention mentioned above are described with reference to FIG. 2 to FIG. 11. FIG. 2 is a perspective view of a first exemplary embodiment of the present invention.

FIG. 2A is a drawing showing an external view of the automatic response/light measurement device 10, which has: an enclosure 11 with a size of 350 mm in depth (Y axis direction), 600 mm in width (X axis direction) and 600 mm in height (Z axis direction), in which the container group 20, the temperature controller 29, the nozzle head 50, the nozzle head transfer mechanism 51, and the CPU+program 60 are built into the interior; a control panel 13 provided on the enclosure 11 having a liquid crystal display portion and operation keys; and a handle 15 that, in addition to being used for opening and closing of the door 17, forms a support member that horizontally supports the door 17 in a case where it is opened.

FIG. 2B is a drawing showing the door 17 opened, a guide rail 19 provided on the rear side of the door 17, and a stage 22 that, in a case where the door 17 is opened and is horizontally placed, is guided by the guide rail 19 and is able to be pulled out onto the rear surface of the door 17.

FIG. 2C is a drawing showing the stage 22 pulled out onto the door 17, and the container group 20 is integrated into the stage 22. The nozzle head 50 is provided on the interior of the enclosure 11. The housing parts for tips and the like 21 are integrated into the stage 22.

Figure 3:
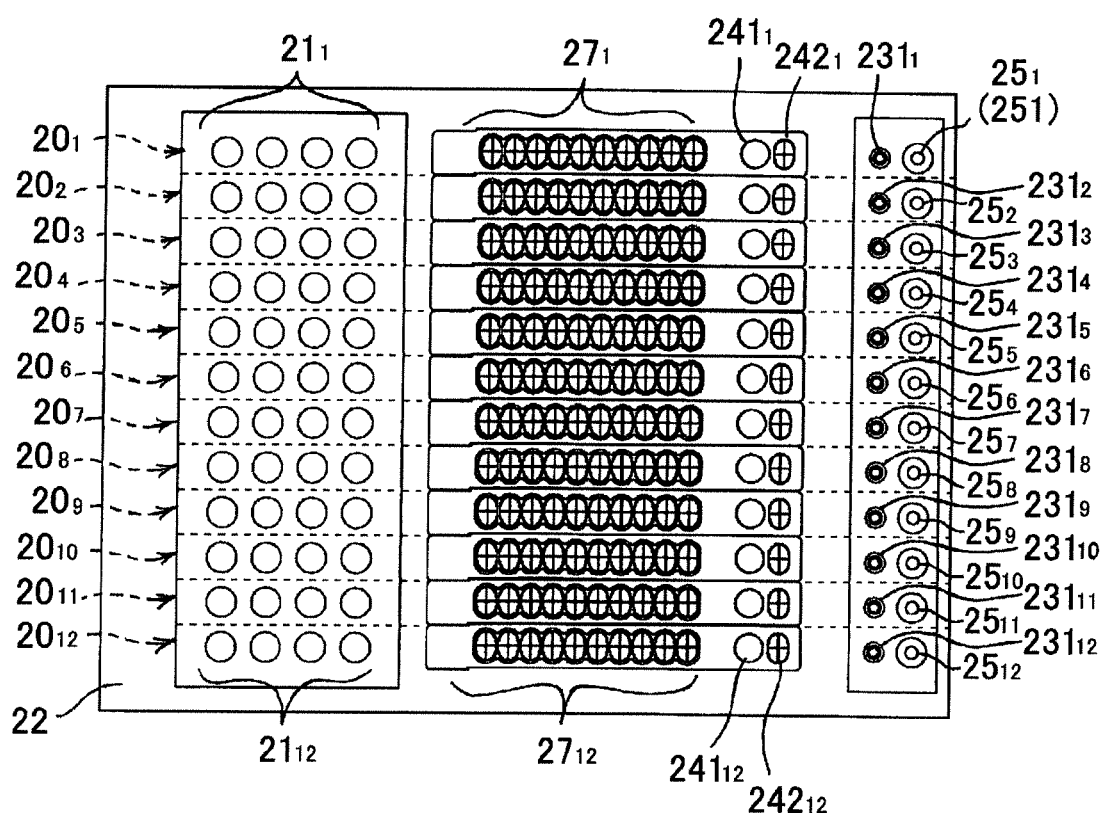
FIG. 3 is a plan view showing enlarged, a container group of the automatic response/light measurement device shown in FIG. 2.

FIG. 3 is a plan view showing enlarged, the container group 20 shown in FIG. 2, which is integrated into the stage 22. The container group 20 is one in which twelve exclusive regions $20_1$-$20_{12}$, wherein the longitudinal direction thereof is along the X axis direction and storage parts are arranged in a single row form, are arranged in parallel along the Y axis direction at a pitch of 18 mm for example. The exclusive regions $20_1$-$20_{12}$ have: a sealing lid storage part $25_1$-$25_{12}$ which houses a single sealing lid $251_1$-$251_{12}$ which has transparency, that is detachably mounted on the twelve coupling ends $31_1$-$31_{12}$ provided on the measurement mount 30; a reaction container $231_1$-$231_{12}$; a reaction tube storage cavity $241_1$-$241_{12}$; a reaction container $242_1$-$242_{12}$; 10 liquid housing part groups $27_1$-$27_{12}$; and housing parts for tips and the like $21_1$-$21_{12}$ that house a sample and one or two or more dispensing tips $211_1$-$211_{12}$.

The capacity of the reaction containers $231_1$-$231_{12}$ is of the order of approximately 200 μL, and the capacity of the other reaction containers, the liquid housing parts, and the tubes is of the order of approximately 2 mL.

The reaction containers $231_1$-$231_{12}$ are used for the amplification of nucleic acids and the fragments thereof, and temperature control is performed by means of the temperature controller 29 based on a predetermined amplification method, such as a thermal cycle (4° C. to 95° C.) for example. The reaction container $231_1$ is formed with two levels as shown in FIG. 6A for example, and has a narrow-mouthed piping part $233_1$ provided on the lower side in which the amplification solution $234_1$ is housed, and a wide-mouthed piping part $232_1$ provided on the upper side, to which the sealing lid $251i$ is fittable. The inner diameter of the wide-mouthed piping part $232_1$ is 8 mm for example. The inner diameter of aperture of the narrow-mouthed piping part $233_1$ is approximately 5 mm for example. The reaction tube housed in the reaction tube storage cavities $241_1$-$241_{12}$, and the reaction containers $242_1$-$242_{12}$ are temperature controlled for incubation in a constant temperature state of 55° C. for example.

The solution for separating and extracting is housed in the liquid housing part group $27_1$-$27_{12}$ as follows. There are 10 liquid housing parts in total in which are respectively stored; 40 μL of Lysis 1 in a first liquid housing part, 200 μL of Lysis 2 in a second liquid housing part, 500 μL of a binding buffer solution in a third liquid housing part, a magnetic particle suspension in a fourth liquid housing part, 700 μL of a washing liquid 1 in a fifth liquid housing part, 700 μL of a washing liquid 2 in a sixth liquid housing part, a dissociation liquid in a seventh liquid housing part, an eighth and a ninth liquid housing part that are empty, and 1.2 mL of distilled water in a tenth liquid housing part, and the reagents, and the like, are prepacked by the apertures thereof being covered by a punchable film.

It is assumed that the housing parts for tips and the like $21_1$-$21_{12}$ retains three dispensing tips $211_1$-$211_{12}$, a tube housing 200 μL of a sample, such as a suspension of bacteria, cells, and the like, or whole blood, and a tube housing 1300 μL of isopropyl alcohol (i-Propanol) as a portion of the solution for separating and extracting proteins used for the removal, and the like, of proteins.

Figure 4:
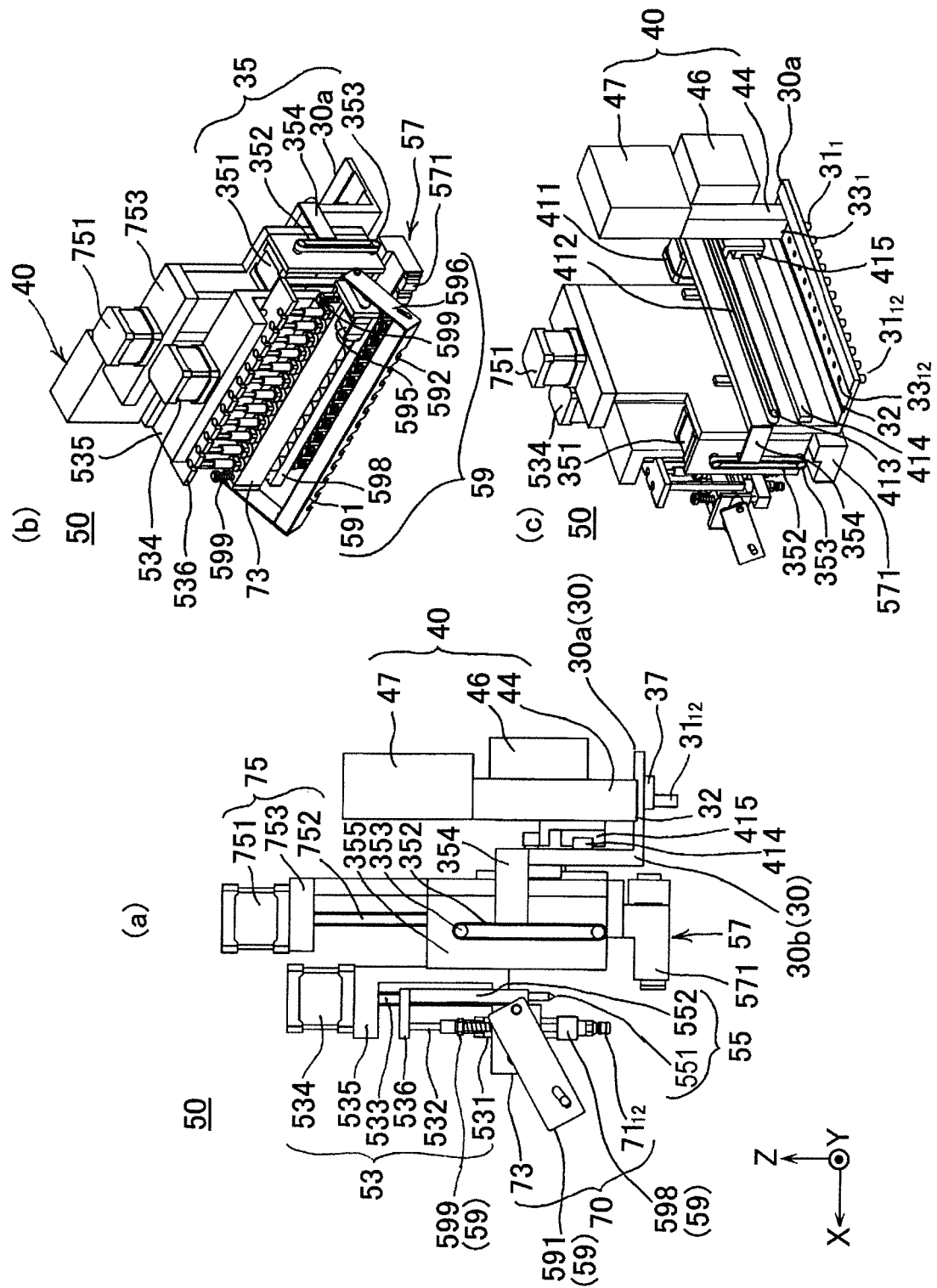
FIG. 4 is a drawing showing enlarged, a whole nozzle head of the automatic response/light measurement device shown in FIG. 2.

FIG. 4 is a drawing showing the nozzle head 50 according to the first exemplary embodiment of the present invention.

The nozzle head 50 has: a nozzle arrangement portion 70; a tip holding-detaching mechanism 59; a suction-discharge mechanism 53; a punching mechanism 55; a magnetic force part 57; a nozzle Z axis transfer mechanism 75; a measurement mount 30; a measuring device 40 provided on the mount 30 having a measuring end 44; an on-mount measuring end transfer mechanism 41 or 411 that moves the measuring end 44 on the mount 30; and a mount Z axis transfer mechanism 35.

The nozzle arrangement portion 70 is provided with a cylinder support member 73 that supports twelve cylinders 531 such that they are arranged along the Y axis direction at a predetermined pitch of 18 mm for example. Furthermore, the downward ends of the cylinders 531 are provided with the nozzles $71_1$-$71_{12}$ such that they are communicated with the cylinders 531.

The tip holding-detaching mechanism 59 has: a tip retaining member 591 in which is provided twelve semicircular notch portions 592 for retaining on the nozzles $71_1$-$71_{12}$ the total of twelve dispensing tips $211_1$-$211_{12}$ mounted on the nozzles $71_1$-$71_{12}$, that extends in the Y axis direction and is formed in a comb shape such that it is axially supported on the cylinder support member 73 via arms 596; and a tip detaching member 598 which is provided with shafts for detaching 599 on both sides, that detaches the twelve dispensing tips $211_1$-$211_{12}$ from the nozzles $71_1$-$71_{12}$.

The suction-discharge mechanism 53 has: the cylinder 531 for performing suction and discharge of gases with respect to the dispensing tips $211_1$-$211_{12}$ which are communicated with the nozzles $71_1$-$71_{12}$ and mounted on the nozzles $71_1$-$71_{12}$, and a piston rod 532 that slides within the cylinder 531; a drive plate 536 that drives the piston rod 532; a ball screw 533 that threads with the drive plate 536; a nozzle Z axis movable body 535 that, in addition to axially supporting the ball screw 533, is integrally formed with the cylinder support member 73; and a motor 534 mounted on the nozzle Z axis movable body 535 that rotatably drives the ball screw 533.

The punching mechanism 55 is provided with punching pins 551 at positions corresponding to the arrangement of the nozzles $71_1$-$71_{12}$, along the lower edge of a square shaped support frame 552 along a vertical surface on a side opposing the side on which the cylinder 531 of the drive plate 536 is provided. The ends of the pins 551 are positioned above the lower ends of the nozzles $71_1$-$71_{12}$ at the time of suction and discharge, and are not lowered past the lower ends of the nozzles $71_1$-$71_{12}$. On the other hand, at the time of punching, although the ends of the punching pins 551 are lowered past the lower ends of the nozzles $71_1$-$71_{12}$ due to the drive plate 536 being lowered past the lower limit of the suction and discharge range, the upper edge of the cylinder 531 is not reached. As a result of this lowering, the punching pins 551 are able to punch the film covering the apertures of the twelve liquid housing part groups $27_1$-$27_{12}$ of the container group 20, which are arranged in a single row form.

The magnetic force part 57 has a magnet 571 that is provided such that it can approach and separate with respect to the narrow diameter portions $211_1a$ of the dispensing tips $211_1$-$211_{12}$ detachably mounted on the nozzles $71_1$-$71_{12}$, and is able to apply and remove a magnetic field in the interior of the dispensing tips $211_1$-$211_{12}$.

The nozzle Z axis transfer mechanism 75 has: a ball screw 752 that threads with the Z axis movable body 535 and vertically moves the Z axis movable body 535 along the Z direction; a nozzle head substrate 753 that axially supports the ball screw 752, and in addition to axially supporting the magnet 57 on the lower side thereof such that it is movable in the X axis direction, is itself movable in the X axis direction by means of the nozzle head transfer mechanism 51 mentioned below; and a motor 751 provided on the upper side of the nozzle head substrate 753 that rotatingly drives the ball screw 752.

The measurement mount 30 comprises a horizontal plate 30a and a vertical plate 30b, which are letter-L shaped plates in cross-section, and is provided with twelve coupling ends $31_1$-$31_{12}$ having light guide portions $33_1$-$33_{12}$, which are directly or indirectly joinable with the apertures of the reaction containers $231_1$-$231_{12}$ and are optically connected with the interior of the reaction containers $231_1$-$231_{12}$, protruding in the downward direction from the horizontal plate 30a. Furthermore, the bases of the coupling ends $31_1$-$31_{12}$ are provided with a heater 37 that heats the sealing lids $251_1$-$251_{12}$ mounted on the coupling ends $31_1$-$31_{12}$ and prevents condensation. The temperature of the heater 37 is set to approximately 105° C. for example. Since the mount 30 is supported by the nozzle head substrate 753 via the nozzle head mount Z axis transfer mechanism 35 such that it is movable in the Z axis direction, it is movable in the nozzle X axis direction and Z axis direction.

The mount Z axis transfer mechanism 35 has: a side plate 355 provided on the nozzle head substrate 753; a mount driving band-shaped member 354 that is supported by a timing belt 352 spanning between two sprockets 353 arranged in the vertical direction axially supported by the side plate 355, and vertically moves in the Z axis direction; and a motor 351 attached to the rear side of the side plate 355 that rotatingly drives the sprockets 353.

A transfer groove 32 is etchingly provided on the horizontal plate 30a of the mount 30 along the Y axis direction such that the upper ends of the light guide portions $33_1$-$33_{12}$ provided on the coupling ends $31_1$-$31_{12}$ are arranged at the bottom thereof. Furthermore, the measuring device 40 is movably provided along the Y axis direction by means of the measuring end 44 of the measuring device 40 being inserted within the groove 32 and sliding. The measuring device 40 is one that supports fluorescence measurements, and has: a light receiving portion 47 that receives the fluorescent light generated in the reaction containers $231_1$-$231_{12}$; an irradiation portion 46 that irradiates the reaction containers $231_1$-$231_{12}$ with an excitation light; and the measuring end 44. Moreover, the measuring end 44 is provided with a light guide portion 43 that is optically connectable to the light guide portions of the coupling ends $31_1$-$31_{12}$.

The vertical plate 30b of the mount 30 is provided with the on-mount measuring end transfer mechanism 41 or 411. The on-mount measuring end transfer mechanism 41 or 411 has: two sprockets 413 on the surface of the vertical plate 30b that are arranged along the Y axis direction; a timing belt 412 spanning between the sprockets 413; a joined portion 415 that is joined with the timing belt 412 and is also joined with the measuring end 44 of the measuring device 40; a guide rail 414 that guides the Y axis direction movement of the joined portion 415; and a motor that rotatingly drives the sprockets 413.

Figure 5:
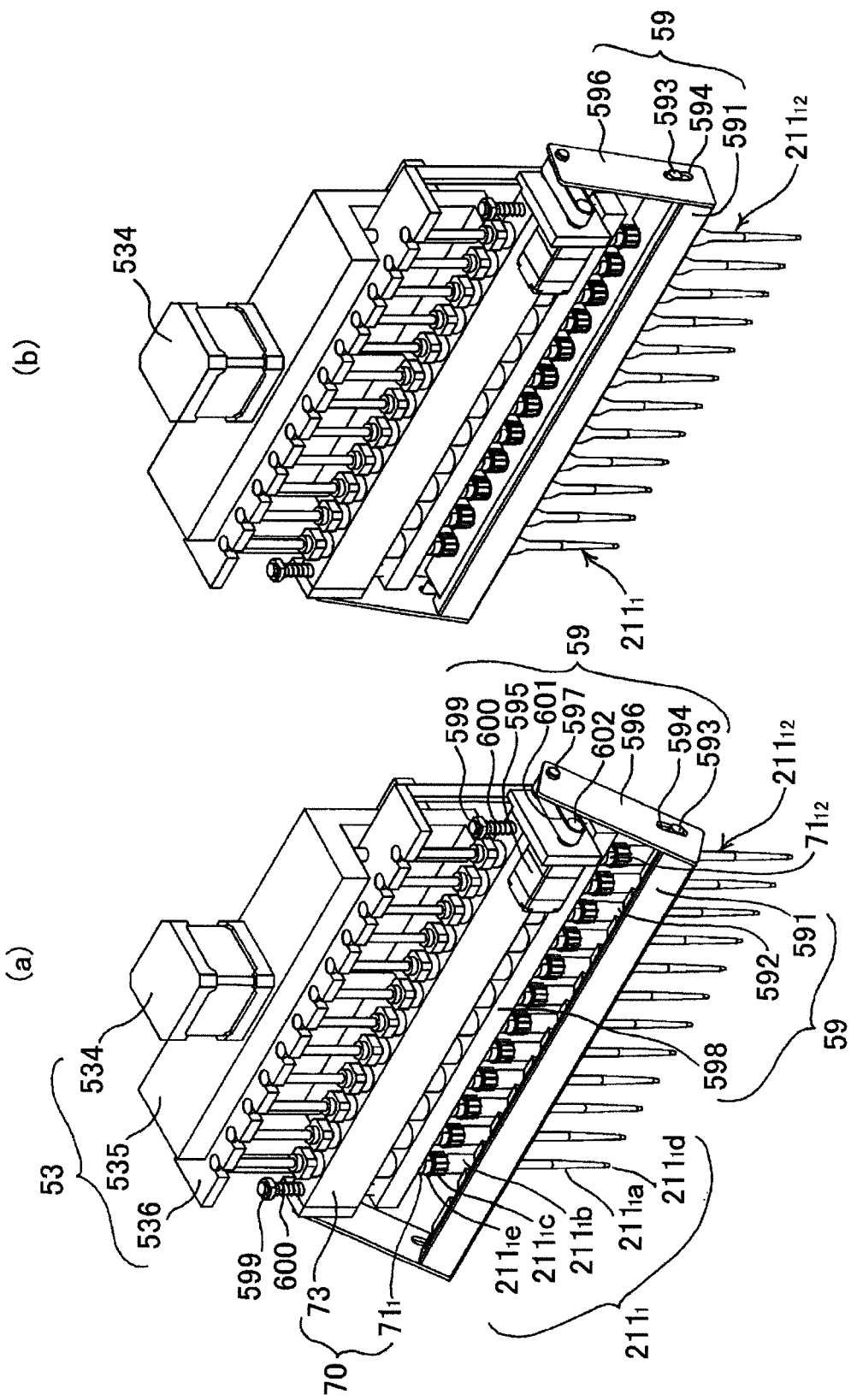
FIG. 5 is a perspective view showing a case where dispensing tips are mounted on nozzles of the device shown in FIG. 2 to FIG. 4.
Figure 6:
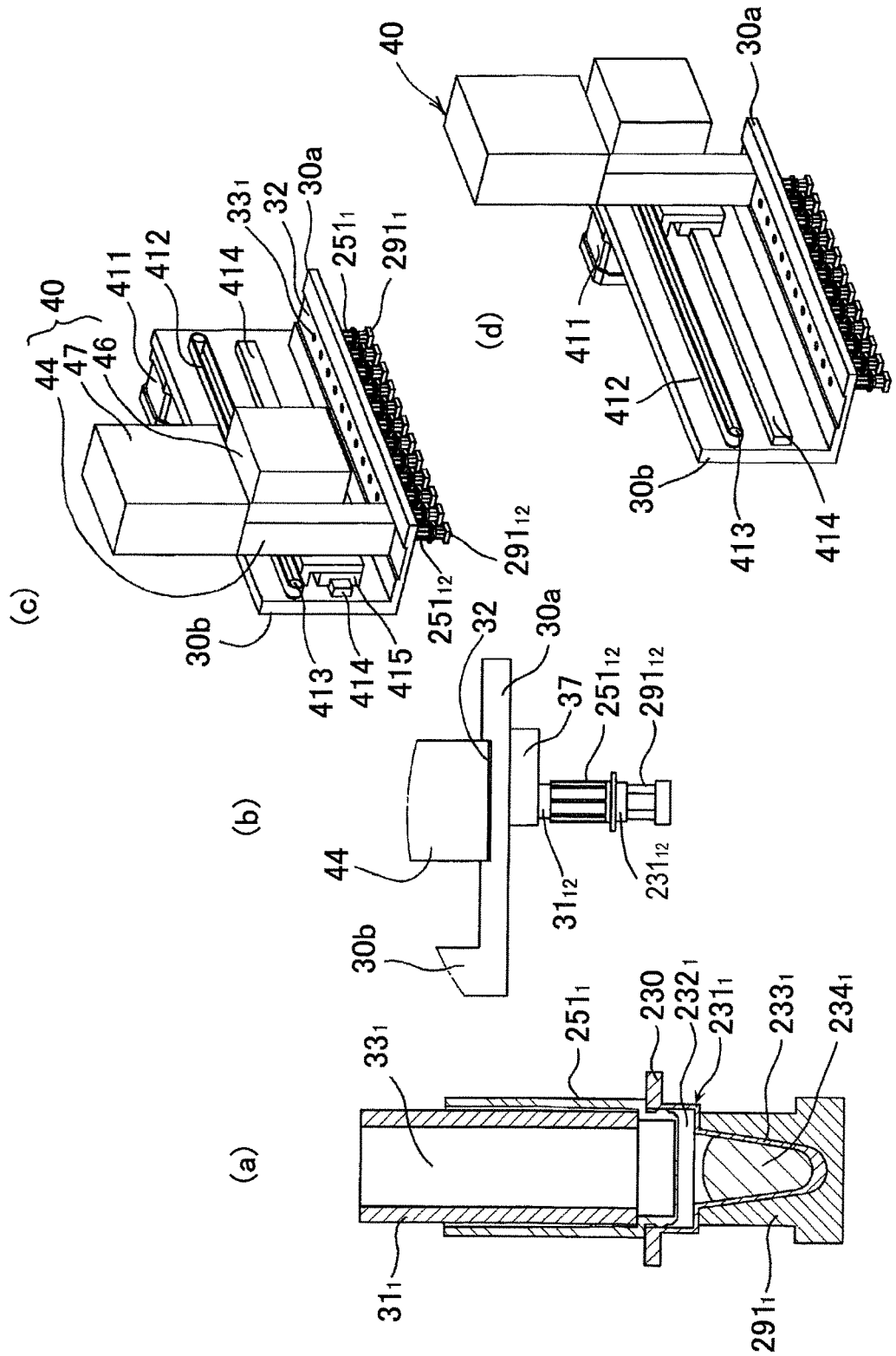
FIG. 6 is a cross-sectional view and a perspective view showing a state in which a coupling end is joined to a reaction container shown in FIG. 3.

FIG. 5 is a drawing showing, at the time the dispensing tips $211_1$-$211_{12}$ are mounted on the nozzles $71_1$-$71_{12}$, the dispensing tips 211i and the operation and the state in which the dispensing tips $211_1$-$211_{12}$ are retained on the nozzles $71_1$-$71_{12}$ using the tip holding-detaching mechanism 59. The dispensing tips $211_1$-$211_{12}$ comprise a narrow diameter portion $211_1a$, a thick diameter portion that has a thicker diameter than the narrow diameter portion $211_1a$, a mounting portion $211_1c$ that as a whole has the largest outer diameter, a mouth portion $211_1d$ at the end in which the inflow and the outflow of liquids is performed, and a mounting aperture $211_1e$ into which the nozzle $71_1$-$71_{12}$ is inserted.

The tip retaining member 591 is provided with twelve semicircular notch portions 592 with an inner diameter smaller than the outer diameter of the mounting portions $211_1c$ of the dispensing tips $211_1$-$211_{12}$ mentioned below, but larger than the outer diameter of the thick diameter portions $211_1b$. The arm 596 is rotatingly driven by a rotating shaft 597 that rotates via a belt 601 by means of a roller 602 that is rotatingly driven by a motor 595.

The tip detaching member 598 is interlocked with the lowering of two tip detaching shafts 599 and detaches the dispensing tips $211_1$-$211_{12}$ from the nozzles $71_1$-$71_{12}$. The tip detaching shaft 599 is elastically supported by the cylinder support member 73 by means of a spring 600 wrapped around the outer periphery such that it is biased in the upward direction, and the upper end thereof is positioned above the upper end of the cylinder 531 but below the lower limit position of the vertical movement range of the normal suction and discharge of a cylinder drive plate 536 mentioned below. The two tip detaching shafts 599 are pushed in the downward direction by means of the cylinder drive plate 536 exceeding the vertical movement range and being lowered near the upper end of the cylinder 531, thus lowering the tip detaching member 598. The tip detaching member 598 has twelve holes having an inner diameter that is larger than the outer diameter of the nozzles $71_1$-$71_{12}$ but smaller than the mounting portions $211_1c$, which represents the largest outer diameter of the dispensing tips $211_1$-$211_{12}$, arranged at the pitch mentioned above such that the nozzles $71_1$-$71_{12}$ pass therethrough.

In a case where the retention of the tips is performed by the tip holding-detaching mechanism 59, following movement of the nozzle head 50, namely of the tip retaining member 591 of the tip holding-detaching mechanism 59 to a position in which it is separated from the nozzles $71_1$-$71_{12}$, and of the arm 596 to the section in which the dispensing tips $211_1$-$211_{12}$ are housed in a state in which it is rotatingly driven, the nozzles $71_1$-$71_{12}$ are lowered by means of the nozzle Z axis transfer mechanism 75 and mounted by being inserted into the apertures $211_1e$. Thereafter, tip retention is performed by rotating the tip retaining member 591 of the tip holding-detaching mechanism 59, and the notch portions 592 making contact with, or approaching, the thick diameter portions $211_1b$ on the lower side of the mounting portions $211_1c$ of the dispensing tips $211_1$-$211_{12}$. At that time, by means of a support shaft 593, which protrudes on both sides of the tip retaining member 591 and is inserted into long holes 594 piercingly provided such that the longitudinal direction thereof is somewhat inclined with respect to the radius of rotation direction of the arm 596, moving within the long holes 594 in the rotation axis direction, the notch portions 592 become positioned at positions directly below the mounting portions 211₁c.

On the other hand, to detach the dispensing tips 211₁-211₁₂ mounted on the nozzles 71₁-71₁₂, after rotating the tip retaining member 591 and separating it from the dispensing tips 211₁-211₁₂, a detaching member 598 is lowered as a result of moving the detaching shaft 599 in the downward direction by lowering the drive plate 536 below the normal suction and discharge position, and the dispensing tips 211₁-211₁₂ become detached from the nozzles 71₁-71₁₂.

FIG. 6A is a drawing showing an example wherein a coupling end 31₁ provided on the mount 30, being a coupling end 31₁ in which a sealing lid 251₁ which has transparency is mounted on the coupling end 31₁, is mounted on the aperture of the reaction container 231₁ of the exclusive region 20₁. The reaction container 231₁ comprises a wide-mouthed piping part 232₁, and a narrow-mouthed piping part 233₁ communicated with the wide-mouthed piping part 232₁, that is formed narrower than the wide-mouthed piping part 232₁. The narrow-mouthed piping part 233₁ is dried beforehand, or houses a liquid form amplification solution 234₁. The wide-mouthed piping part 232₁ and the narrow-mouthed piping part 233₁ are integrally joined with the base portion 230 of the container. Here, for the reagent for real-time amplification, 70 μL of a master mix (SYBR (registered trademark) Green Mix) consisting of enzymes, buffers, primers, and the like, is housed beforehand.

The aperture of the wide-mouthed piping part 232₁ has a size into which the end of the sealing lid 251₁ which has transparency, is fittable. Further, the coupling end 31₁ has a size in which it is fittable within the sealing lid 251₁. At the time of fitting, it is preferable for the diameter of the light guide portion 33₁, which passes the interior of the coupling end 31₁, to be the same as the size of the diameter of the aperture of the narrow-mouthed piping part 233₁ or larger. Consequently, it becomes possible to receive the light from the reaction container 231₁ with certainty. The narrow-mouthed piping part 233₁ is housed within a temperature control block 291₁ that is heated or cooled by a temperature controller 29.

FIG. 6B is a drawing showing a state in which the coupling end 31₁₂, which protrudes from the horizontal plate 30a of the mount 30 to the lower side, is joined with the reaction container 231₁₂ in a state in which it is fitted to the sealing lid 251₁₂. FIG. 6C and FIG. 6D are drawings showing an operation in which the measuring device 40 moves on the mount 30. This operation is one in which, while moving along the groove 32 by means of the on-mount measuring end transfer mechanism 41 or 411 in a state in which the measuring end 44 is inserted into the groove 32, the light guide portions 33₁-33₁₂ of the twelve coupling ends 31₁-31₁₂ arranged in the groove 32 and the light guide portion 43 of the measuring end 44 are successively optically connected. The speed of the measuring end 44, and therefore the measuring device 40, on the measurement mount 30 is determined by considering the stable light receivable time, the number of reaction containers, the pitch, and the like, and is controlled such that it becomes 100 mm to 500 mm per second in the case of a real-time PCR measurement for example. In the present exemplary embodiment, since the measuring end 44 moves by sliding within the groove 32, optical noise incident to the lower end surface of the measuring end 44 can be prevented.

Figure 7:
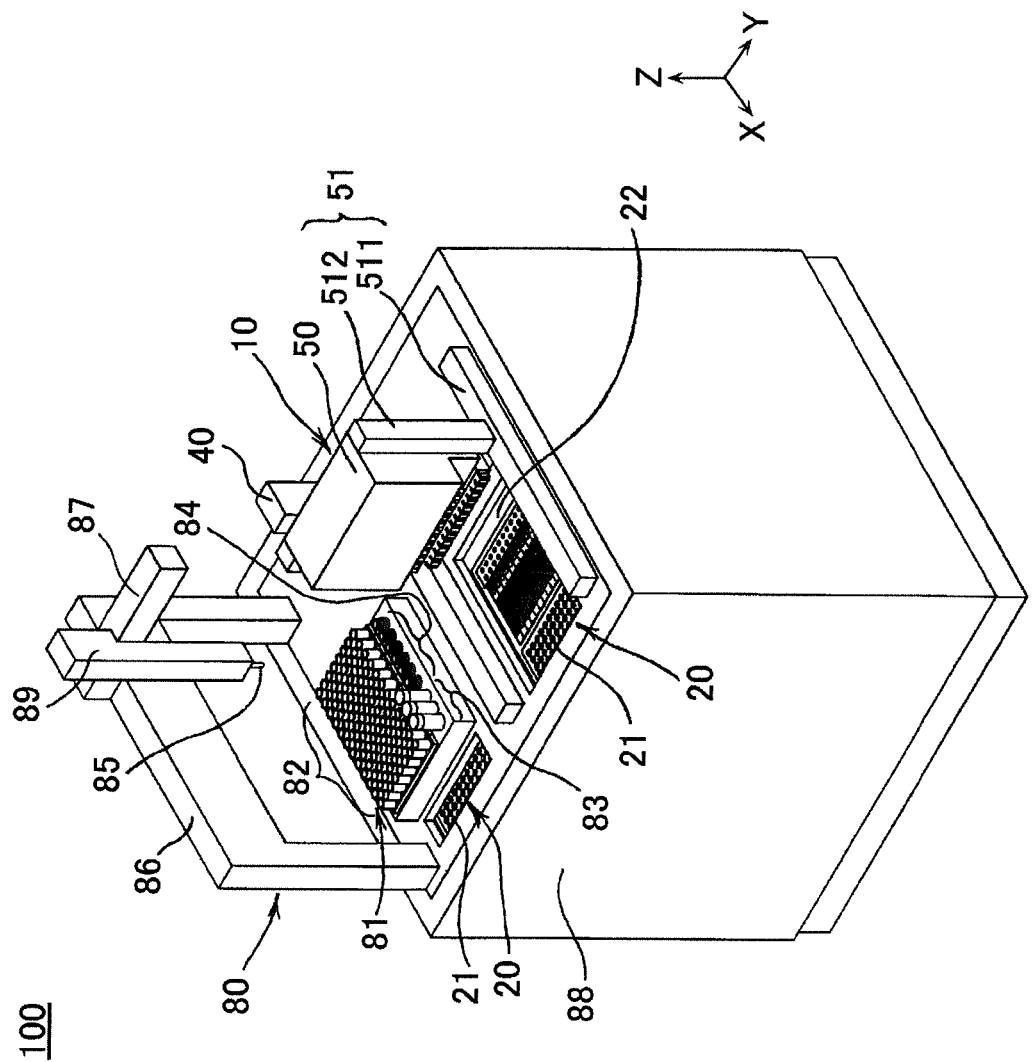
FIG. 7 is a perspective view showing a second exemplary embodiment of the automatic response/light measurement device shown in FIG. 1.

FIG. 7 is a perspective view showing an automatic response/light measurement device 100 according to a second exemplary embodiment.

The device 100 comprises a section corresponding to the automatic response/light measurement device 10 according to the first exemplary embodiment, which has the nozzle head 50, the nozzle head transfer mechanism 51, and the container group 20 built into the stage 22, and a feeding device for samples and the like 80.

Here, the nozzle head transfer mechanism 51 is a mechanism that has a timing belt 511 and a joined portion 512 that joins to it, and makes the nozzle head 50 movable in the X axis direction, and is the same as in the automatic response/light measurement device 10 according to the first exemplary embodiment.

On the other hand, the feeding device for samples and the like 80 is a device for supplying parent samples, and the like, with respect to the container group 20 by dispensing, and the stage 22, to which the container group 20 supplied with the parent samples and the like, is built-in, becomes automatically moved to the automatic response/light measurement device. It has: a parent container group 81 which houses the parent samples and the like; a nozzle head 89 having a tip detaching mechanism, a suction-discharge mechanism, and a single nozzle 85 that, in addition to the suction and discharge of gases being performed by means of the mechanisms, has a dispensing tip 211₁-211₁₂ detachably mounted, that has a mechanism that moves along the Z axis direction with respect to the parent container group 81 and the housing parts for tips and the like 21 of the container group 20; an X axis movable body 87 having a Y axis transfer mechanism that moves the nozzle head 89 in the Y axis direction with respect to the parent container group 81 and the like; an X axis transfer mechanism 86 that moves the X axis movable body 87 along the X axis direction with respect to the parent container group 81 and the like; and the parent container group 81. The parent container group 81 has: a parent sample storage part group 82 arranged in a 12 row×8 column matrix form that houses the parent samples to be supplied to the housing parts for tips and the like 21 of the container group 20; a distilled water/washing liquid group 83; and a reagent bottle group 84. Reference symbol 88 represents a seat portion of the device 100.

The feeding device for samples and the like 80 moves the nozzle head 89 to a storage part of the container group 20 housing a dispensing tip 211₁-211₁₂, then by lowering mounts the dispensing tip 211₁-211₁₂ on the nozzle 85 thereof, and by using the Z axis transfer function of the nozzle head 89, the X axis transfer mechanism 86, and the Y axis transfer function of the X axis movable body 87, moves to the corresponding parent sample storage part of the parent sample storage part group 82, aspirates the sample, and transfers it to the corresponding storage part of the housing parts for tips and the like 21₁-21₁₂ of the container group 20. The dispensing tip 211₁-211₁₂, in which the transfer is completed, is detached into the storage part by the tip detaching portion. The necessary washing liquids, reagents, and the like, become supplied to the housing parts for tips and the like 21₁-21₁₂ by the same method using other dispensing tips 211₁-211₁₂.

Figure 8:
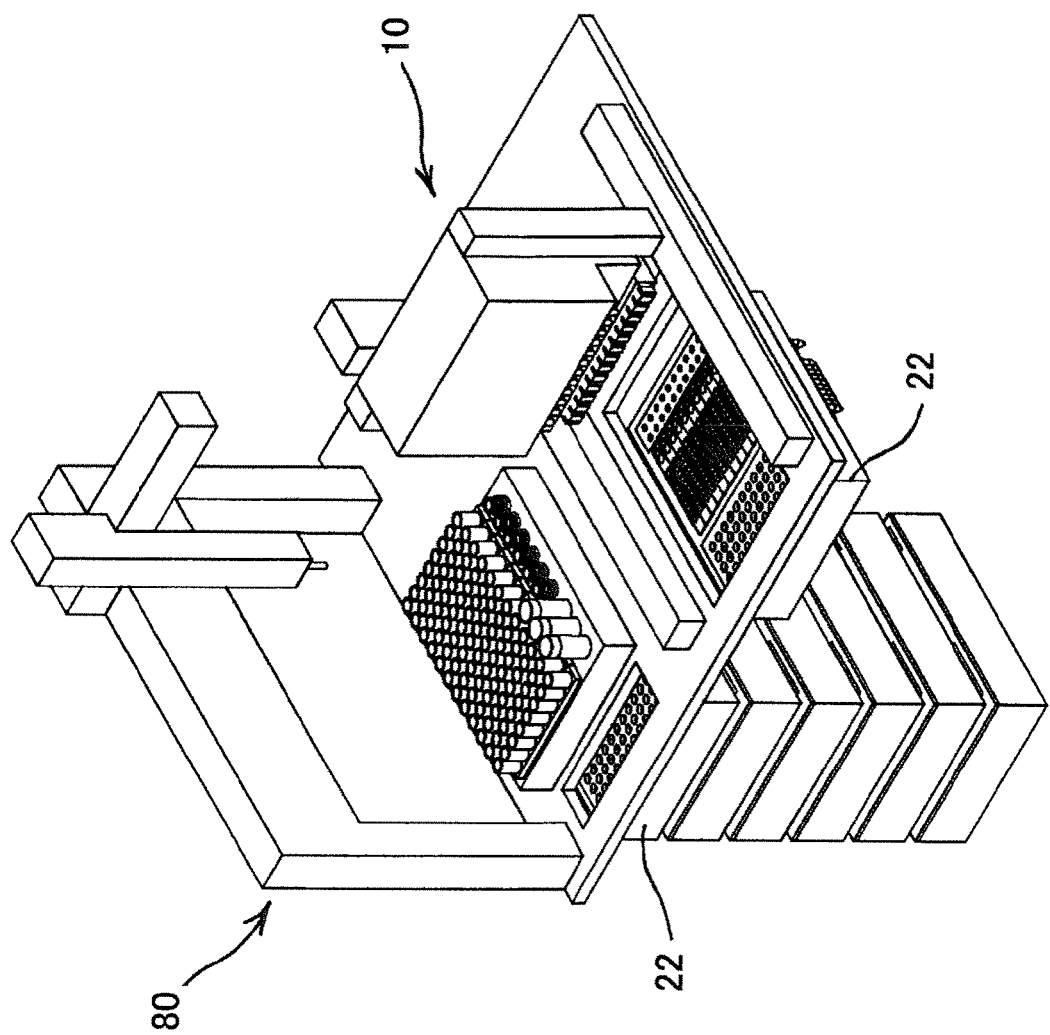
FIG. 8 is a plan view showing enlarged, a container group of the automatic response/light measurement device shown in FIG. 7.

FIG. 8 is a drawing showing the interior of the seat portion 88, in which a plurality of stages 22 are layered on the lower side of the feeding device for samples and the like 80. Furthermore, when the sample feeding process is completed with respect to the stage 22 of the uppermost level, and the stage 22 moves along the Y axis direction and is positioned on the lower side of the automatic response/light measurement device 10, since the stages 22 on the lower side are biased by an elastic force and the like, they successively become moved to the upper level side. Consequently, rapid and efficient processing can be performed.

Figure 9:
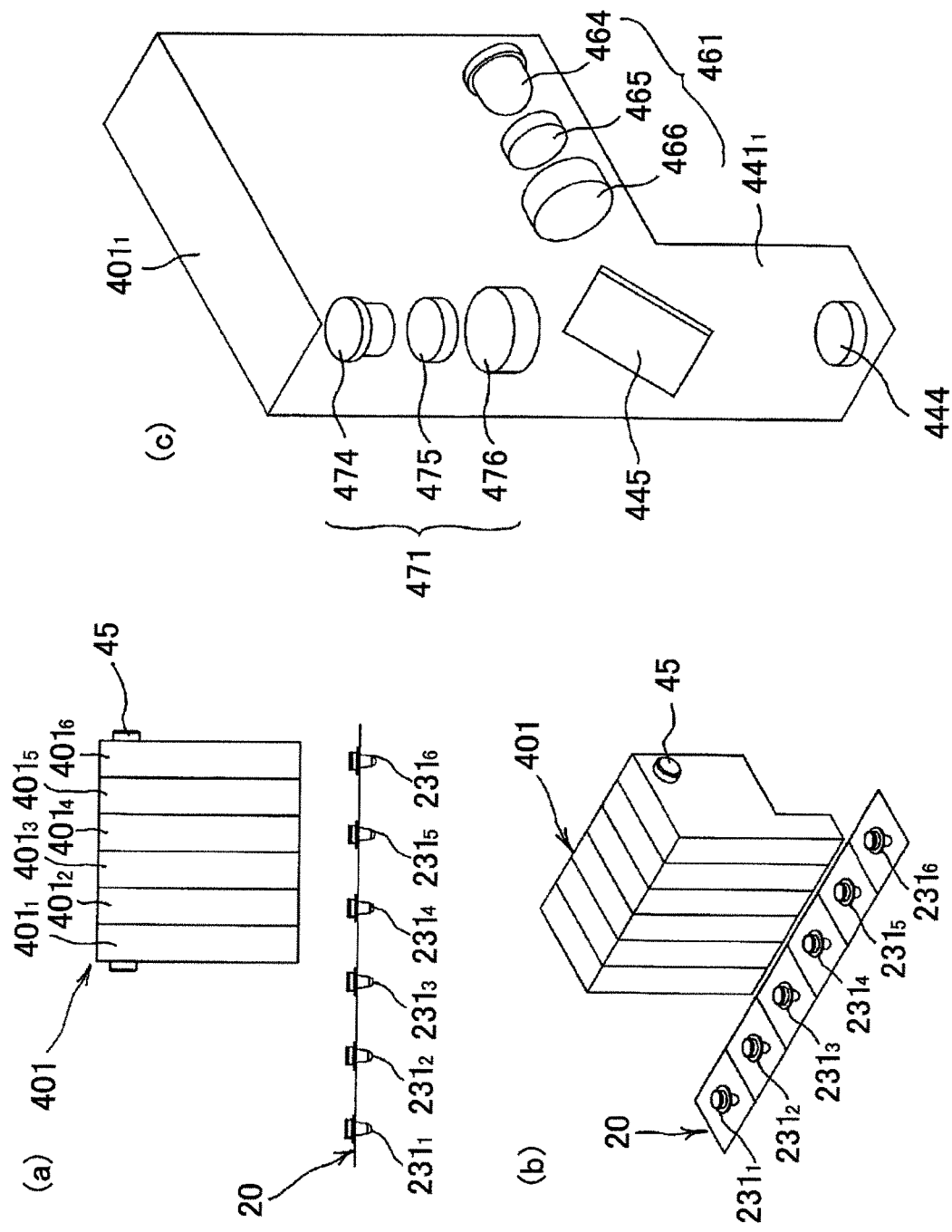
FIG. 9 is a drawing showing a measuring device according to a third exemplary embodiment of the present invention.

FIG. 9 is a drawing showing a measuring device 401 according to a third exemplary embodiment of the present invention.

The measuring device 401 is one in which a plurality (six in this example) of specific wavelength measuring devices $401_1$-$401_6$ are, including the measuring ends 441, integrally joined in parallel and in a single row form. Reference symbol 45 represents a shaft that serves as a measuring end bundling portion for integrally bundling together the specific wavelength measuring devices $401_1$-$401_6$. This shaft is one that penetrates the holes piercingly provided in the specific wavelength measuring devices $401_1$-$401_6$, which have an inner diameter that is somewhat larger than the outer diameter of the shaft, and joins these by tightening screw type end portions having a sufficiently larger outer diameter than the holes.

The pitch of the specific wavelength measuring devices $401_1$-$401_6$ in the movement direction, assuming a pitch between the reaction containers $231_1$-$231_{12}$ of the container group 20 or the end portions of the light guide portions $33_1$-$33_{12}$ of the coupling ends $31_1$-$31_{12}$ on the mount 30 of 18 mm, is 9 mm, which is half thereof. Therefore, the on-mount measuring end transfer mechanism 41 or 411 moves the measuring ends $441_1$-$441_6$ of the specific wavelength measuring devices $401_1$-$401_6$ intermittently such that they momentarily stop at each pitch advance, or continuously.

FIG. 9C is a drawing showing the interior of the specific wavelength measuring device 401j. The measuring device $401_1$-$401_6$ has: a measuring end 441 in which a lens 444, wherein excitation light exits to the reaction container $231_1$-$23_{16}$ and fluorescent light from the reaction containers $231_1$-$23_{16}$ is incident, and a dichroic mirror 445 are provided to a light guide portion; an irradiation portion 461 having a filter 466, a lens 465, and an LED 464 for irradiating excitation light; and a light receiving portion 471 having a filter 476, a lens 475 and a photodiode 474.

According to the third exemplary embodiment of the present invention, the light from the LED 464 is such that the excitation light of a specific wavelength band that passes the filter 466 is reflected by the dichroic mirror 445 and is irradiated through the lens 444 of the measuring end 441 and into the reaction containers $231_1$-$231_{12}$, and the fluorescent light excited by the excitation light passes the lens 444 of the measuring end 441, is transmitted through the dichroic mirror 445, and the fluorescent light of a predetermined specific wavelength selected by the filter 476 passes the lens 475, and is incident to the photodiode 474 and is received. The fluorescent light of other wavelengths is also successively received using the six specific wavelength measuring devices $403_1$-$403_6$.

Figure 10:
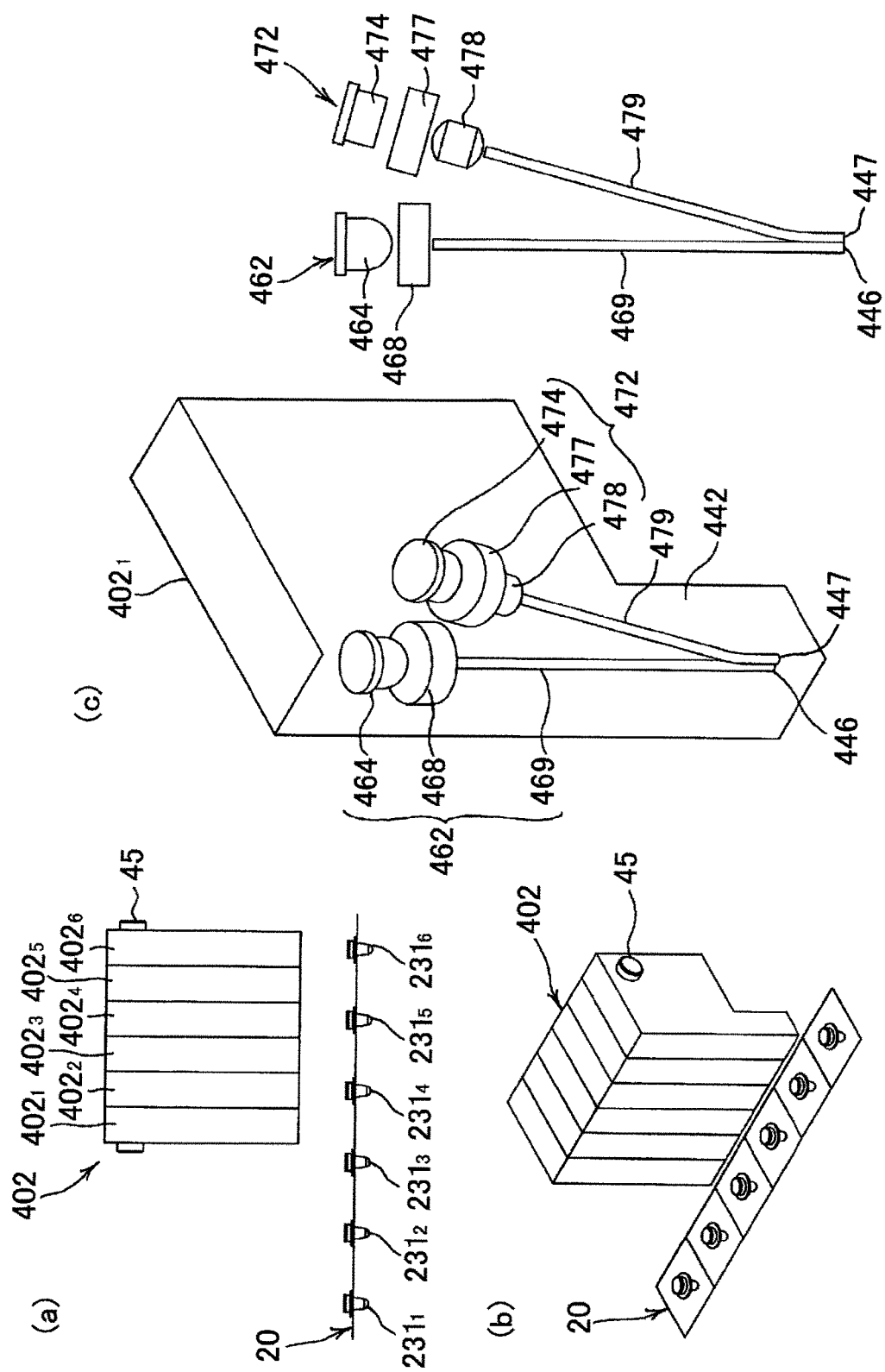
FIG. 10 is a drawing showing a measuring device according to a fourth exemplary embodiment of the present invention.

FIG. 10 is a drawing showing a measuring device 402 according to a fourth exemplary embodiment of the present invention.

The measuring device 402 is one in which a plurality (six in this example) of specific wavelength measuring devices $402_1$-$402_6$ are, including the measuring ends 442, integrally joined in parallel and in a single row form. The specific wavelength measuring devices $402_1$-$402_6$ differ from the specific wavelength measuring devices $401_1$-$401_6$ according to the third exemplary embodiment mentioned above with regard to the interior thereof, as shown in FIG. 10C.

The specific wavelength measuring device $402_1$-$402_6$ according to the present exemplary embodiment has: a measuring end 442 that, in addition to having an optical fiber 469 for the excitation light to exit to the reaction container $231_1$-$231_{12}$ and an optical fiber 479 for the light from the reaction container $231_1$-$231_{12}$ to be incident, is provided with an irradiation end 446 of the optical fiber 469 and a light receiving end 447 of the optical fiber 479 on the lower end; an LED 467 that irradiates excitation light through the optical fiber 469; an irradiation portion 462 having a filter 468; and a light receiving portion 472 having the optical fiber 479, a drum lens 478, a filter 477 and a photodiode 474.

Figure 11:
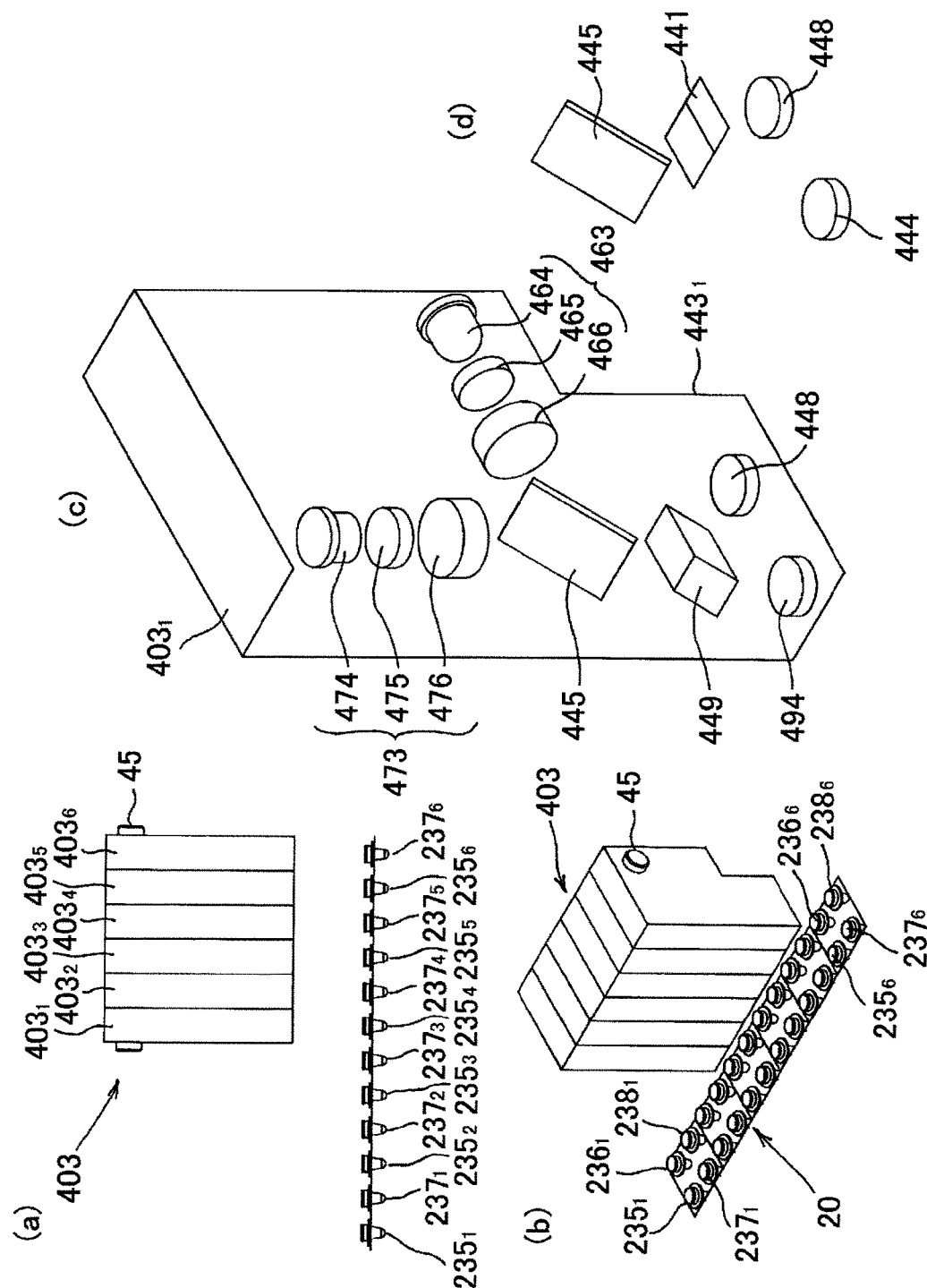
FIG. 11 is a drawing showing a measuring device according to a fifth exemplary embodiment of the present invention.

FIG. 11 is a drawing showing a measuring device 403 according to a fifth exemplary embodiment of the present invention.

The measuring device 403 is one in which each of the exclusive regions $20_1$-$20_{12}$ has four reaction containers $235_1$-$235_6$, $236_1$-$236_6$, $237_1$-$237_6$, and $238_1$-$238_6$, and the reaction container groups $23_1$-$23_{12}$ comprise in the X axis direction with respect to the movement direction (Y axis direction) of the measuring device 403, two rows comprising the reaction container row $235_1$-$235_6$, $237_1$-$237_6$ and the reaction container row $236_1$-$236_6$, $238_1$-$238_6$ at a spacing of 9 mm pitch for example.

The measuring device 403 is one in which a plurality (six in this example) of specific wavelength measuring devices $403_1$-$403_6$ are, including the measuring ends 443, integrally joined in parallel and in a single row form. The specific wavelength measuring devices $403_1$-$403_6$ differ from the measuring devices $401_1$-$401_6$ and $402_1$-$402_6$ mentioned above with regard to the interior thereof, as shown in FIG. 11C.

FIG. 11C is a drawing showing the interior of the measuring device 403j according to the present exemplary embodiment. The measuring device $403_1$-$403_6$ has: a measuring end $443_1$-$443_6$ having a lens 444, wherein excitation light exits to the reaction container $235_1$-$235_6$ or the reaction container $237_1$-$237_6$ and fluorescent light from the reaction container $235_1$-$235_6$ or the reaction container $237_1$-$237_6$ is incident, and a lens 448, wherein excitation light exits to the reaction container $236_1$-$236_6$ or the reaction container $238_1$-$238_6$ and fluorescent light from the reaction container $236_1$-$236_6$ or the reaction container $238_1$-$238_6$ is incident, a dichroic mirror 445, and a rotatable rhombic prism 449 for switching to either a light guide portion that connects the dichroic mirror 445 and the lens 444 or a light guide portion that connects the lens 448 and the dichroic mirror 445; an irradiation portion 463 having a filter 466, a lens 465, and an LED 464 for irradiating excitation light; and a light receiving portion 473 having a filter 476, a lens 475, and a photodiode 474.

The position of the rhombic prism 449 in FIG. 11C represents a case where the incidence and exiting of the light is performed with respect to the reaction containers $235_1$-$235_6$ or $237_1$-$237_6$ via the lens 444. Furthermore, the position of the rhombic prism 449 in FIG. 11D represents a case where the incidence and exiting of the light is performed with respect to the reaction container $236_1$-$236_6$ or the reaction container $238_1$-$238_6$ via the lens 448.

The speed of the measuring ends 441, 442, and 443, and therefore the measuring devices 401, 402, and 403 with respect to the container group 20 or the measurement mount 30 is approximately 100 mm to 500 mm for example.

Next, a series of processing operations that perform real-time PCR of the nucleic acids of a sample containing bacteria using the automatic response/light measurement device 10 according to the first exemplary embodiment is described. Step S1 to step S13 below correspond to separation and extraction processing.

In step S1, the door 17 of the automatic response/light measurement device 10 shown in FIG. 2 is opened, the stage 22 is pulled out, and by utilizing the feeding device for samples and the like 80 for example, which is separately provided from the container group 20 and on the stage 22, the samples, which are subject to testing, various washing liquids, and various reagents, are supplied beforehand, and furthermore, a liquid housing part in which the reagents and the like are prepacked is mounted.

In step S2, following returning of the stage 22 and closing of the door 17, the start of the separation and extraction and amplification processing is instructed by means of the operation of the touch panel of the control panel 13 for example.

In step S3, the extraction control part 65 provided to the nucleic acid processing controller 63 of the CPU+program 60 of the automatic response/light measurement device 10 instructs the nozzle head transfer mechanism 51 and moves the nozzle head 50 in the X axis direction, positions the punching pin 551 above the first liquid housing part of the liquid housing part group $27_1$-$27_{12}$ of the container group, and punches the film covering the aperture of the liquid housing part by lowering the drive plate 536 of the suction-discharge mechanism 53 past the lower limit of the suction and discharge range, and in the same manner, the other liquid housing parts of the liquid housing part group $27_2$-$27_{12}$ and the reaction container group $23_1$-$23_{12}$ are successively punched by moving the nozzle head 50 in the X axis direction and using the suction-discharge mechanism 53.

In step S4, the nozzle head 50 is again moved in the X axis direction and moved to the housing parts for tips and the like $21_1$-$21_{12}$, and the nozzles $71_1$-$71_{12}$ are lowered by means of the nozzle Z axis transfer mechanism 75, and the dispensing tips $211_1$-$211_{12}$ are mounted. Next, by bringing the tip retaining member 591 of the tip holding-detaching mechanism 59 with the thick diameter portions $211_1b$-$211_{12}b$ of the dispensing tips $211_1$-$211_{12}$, the dispensing tips $211_1$-$211_{12}$ are retained on the nozzles $71_1$-$71_{12}$ and detachment is prevented. Following raising by the nozzle Z axis transfer mechanism 75, the dispensing tip $211_1$-$211_{12}$ is moved along the X axis by means of the nozzle head transfer mechanism 51, and after it reaches the tenth liquid housing part of the liquid housing part group $27_1$-$27_{12}$, it is loweringly inserted into the narrow diameter portion $211_1a$-$211_{12}a$ of the dispensing tip $211_1$-$211_{12}$ by the nozzle Z axis transfer mechanism 75. Then, 50 μL of distilled water is aspirated by means of the suction-discharge mechanism 53, and following raising of the dispensing tip $211_1$-$211_{12}$ above the liquid housing part again, the dispensing tip $211_1$-$211_{12}$ is moved by the nozzle head transfer mechanism 51, and the distilled water is discharged within the eighth liquid housing part and housed as a dissociation liquid. In the same manner, 350 μL of distilled water is housed in the sixth liquid housing part.

In step S5, furthermore to the solution components (NaCl, SDS solutions) housed beforehand in the third liquid housing part and the fifth liquid housing part, and to the distilled water housed in the sixth liquid housing part, as mentioned above, a predetermined amount of isopropyl alcohol (i-Propanol) is aspirated from the tube, and predetermined amounts are respectively dispensed to the third liquid housing part, the fifth liquid housing part, and the sixth liquid housing part. By so doing, 500 μL of a binding buffer solution (NaCl, SDS, i-Propanol), 700 μL of a washing liquid 1 (NaCl, SDS, i-Propanol), and 700 μL of washing liquid 2 (water 50%, i-Propanol 50%) are respectively prepared as solutions for separating and extracting within the third, the fifth, and the sixth liquid housing parts.

In step S6, following movement to, among the housing parts for tips and the like $21_1$-$21_{12}$, the sample tube in which the sample is housed, the narrow diameter portion $211_1a$ of the dispensing tip $211_1$-$211_{12}$ is loweringly inserted using the nozzle Z axis transfer mechanism 75, and, with respect to the suspension of the sample housed in the sample tube, following suspension of the sample within the liquid by repeating the suction and the discharge by raising and lowering the drive plate 536 of the suction-discharge mechanism 53, the sample suspension is aspirated within the dispensing tip $211_1$-$211_{12}$. The sample suspension is moved along the X axis by means of the nozzle head transfer mechanism 51 to the first liquid housing part of the liquid housing part group $27_1$-$27_{12}$ housing the Lysis 1 (enzyme) representing the solution for separating and extracting, and the narrow diameter portion $211_1a$ of the dispensing tip $211_1$-$211_{12}$ is inserted through the hole in the punched film, and the suction and the discharge is repeated in order to stir the sample suspension and the Lysis 1.

In step S7, the entire amount of the stirred liquid is aspirated by the dispensing tip $211_1$-$211_{12}$, and incubation is performed by housing it in the reaction tube retained in the storage cavity $241_1$-$241_{12}$ that is set to 55° C. by means of the constant temperature controller. Consequently, the protein contained in the sample is broken down and made a low molecular weight. After a predetermined time has elapsed, the reaction mixture is left in the reaction tube, the dispensing tip $211_1$-$211_{12}$ is moved to the second liquid housing part of the liquid housing part group $27_1$-$27_{12}$ by means of the nozzle head transfer mechanism 51, and the entire amount of the liquid housed within the second liquid housing part is aspirated by using the nozzle Z axis transfer mechanism 75 and the suction-discharge mechanism 53, and it is transferred using the dispensing tip $211_1$-$211_{12}$ by means of the nozzle head transfer mechanism 51, and the reaction solution is discharged within the third liquid housing part by penetrating the hole in the film and inserting the narrow diameter portion.

In step S8, the binding buffer solution housed within the third liquid housing part, which represents a separation and extraction solution, and the reaction solution are stirred, the solubilized protein is further dehydrated, and the nucleic acids or the fragments thereof are dispersed within the solution.

In step S9, using the dispensing tip $211_1$-$211_{12}$, the narrow diameter portion thereof is inserted into the third liquid housing part by passing through the hole in the film, the entire amount is aspirated and the dispensing tip $211_1$-$211_{12}$ is raised by means of the nozzle Z axis transfer mechanism 75, and the reaction solution is transferred to the fourth liquid housing part, and the magnetic particle suspension housed within the fourth liquid housing part is stirred with the reaction solution. A cation structure in which Na+ ions bind to the hydroxyl groups formed on the surface of the magnetic particles contained within the magnetic particle suspension is formed. Consequently, the negatively charged DNA is captured by the magnetic particles.

In step S10, the magnetic particles are adsorbed on the inner wall of the narrow diameter portion $211_1a$ of the dispensing tip $211_1$-$211_{12}$ by approaching the magnet 571 of the magnetic force part 57 to the narrow diameter portion $211_1$-$211_{12}$ of the dispensing tip $211_1$-$211_{12}$. In a state in which the magnetic particles are adsorbed on the inner wall of the narrow diameter portion $211_1a$ of the dispensing tip $211_1$-$211_{12}$, the dispensing tip $211_1$-$211_{12}$ is raised by means of the nozzle Z axis transfer mechanism 75 and moved from the fourth liquid housing part to the fifth liquid housing part using the nozzle head transfer mechanism 51, and the narrow diameter portion 211₁$a$ is inserted by passing through the hole in the film.

In a state in which the magnetic force within the narrow diameter portion 211₁$a$ is removed by separating the magnet 571 of the magnetic force part 57 from the narrow diameter portion 211₁$a$ of the dispensing tip 211₁-211₁₂, as a result of repeating the suction and the discharge of the washing liquid 1 (NaCl, SDS, i-Propanol) housed in the fifth liquid housing part, the magnetic particles are released from the inner wall, and the protein is washed by stirring within the washing liquid 1. Thereafter, in a state in which the magnetic particles are adsorbed on the inner wall of the narrow diameter portion 211₁$a$ as a result of approaching the magnet 571 of the magnetic force part 57 to the narrow diameter portion 211₁$a$ of the narrow diameter portion 211₁$a$ again, the dispensing tip 211₁-211₁₂ is, by means of the nozzle Z axis transfer mechanism 75, moved from the fifth liquid housing part to the sixth liquid housing part by means of the nozzle head transfer mechanism 51.

In step S11, the narrow diameter portion 211₁$a$ of the dispensing tip 211₁-211₁₂ is inserted by passing through the hole in the film using the nozzle Z axis transfer mechanism 75. By repeating the suction and the discharge of the washing liquid 2 (i-Propanol) housed in the sixth liquid housing part in a state in which the magnetic force within the narrow diameter portion 211₁$a$ is removed by separating the magnet 571 of the magnetic force part 57 from the narrow diameter portion 211₁$a$ of the dispensing tip 211₁-211₁₂, the magnetic particles are stirred within the liquid, the NaCl and the SDS is removed, and the protein is washed. Thereafter, in a state in which the magnetic particles are adsorbed on the inner wall of the narrow diameter portion 211₁$a$ by approaching the magnet 571 of the magnetic force part 57 to the narrow diameter portion 211₁$a$ of the dispensing tip 211₁-211₁₂ again, the dispensing tip 211₁-211₁₂ is, following raising by means of the nozzle Z axis transfer mechanism 75, moved from the sixth liquid housing part to the ninth liquid housing part, in which the distilled water is housed, by means of the nozzle head transfer mechanism 51.

In step S12, by means of the nozzle Z axis transfer mechanism 75, the narrow diameter portion 211₁$a$ of the dispensing tip 211₁-211₁₂ is lowered through the hole, and by repeating the suction and the discharge of the water at a slow flow rate in a state in which the magnetic force is applied within the narrow diameter portion 211₁$a$ of the dispensing tip 211₁-211₁₂, the i-Propanol is substituted by water and is removed.

In step S13, by means of the nozzle head transfer mechanism 51, the dispensing tip 211₁-211₁₂ is moved along the X axis direction and the narrow diameter portion 211₁$a$ is inserted into the eighth liquid housing part through the hole in the film. By stirring the magnetic particles by repeating the suction and the discharge within the distilled water, which represents the dissociation liquid, in a state in which the magnet 571 of the magnetic force part 57 is separated from the narrow diameter portion 211₁$a$ of the dispensing tip 211₁-211₁₂ and the magnetic force is removed, the nucleic acids or the fragments thereof retained by the magnetic particles are dissociated (eluted) from the magnetic particles into the liquid. Thereafter, a magnetic field is applied within the narrow diameter portion and the magnetic particles are adsorbed on the inner wall by approaching the magnet 571 to the narrow diameter portion 211₁$a$ of the dispensing tip 211₁-211₁₂, and the solution containing the extracted nucleic acids, and the like, is made to remain in the eighth liquid housing part. The dispensing tip 211₁-211₁₂ is moved to the storage part of the housing parts for tips and the like 21₁-21₁₂ in which the dispensing tip 211₁-211₁₂ was housed, by means of the nozzle head transfer mechanism 51, and following separation of the tip retaining member 591 of the tip holding-detaching mechanism 59 from the dispensing tip 211₁-211₁₂, the dispensing tip 211₁-211₁₂ to which magnetic particles are adsorbed, is detached from the nozzle 181 together with the magnetic particles and dropped into the storage part, using the detaching member 598.

The following step S14 to step S17 corresponds to nucleic acid amplification and measurement processing.

In step S14, the nozzle head 50 is moved by means of the nozzle head transfer mechanism 51, and the coupling end 31₁-31₁₂ of the measurement mount 30 is moved above the sealing lid storage part 25$i$ housing the sealing lids 251 of the container group 20. The sealing lid 251 is mounted by fitting to the lower end of the coupling end 31₁-31₁₂ by being lowered using the mount Z axis transfer mechanism 35. After being raised by the mount Z axis transfer mechanism 35, the coupling end 21₁-21₁₂ mounted with the sealing lid 251 is positioned on the reaction container 231₁-231₁₂ using the nozzle head transfer mechanism 51, and by lowering the coupling end 31₁-31₁₂ mounted with the sealing lid 251 by means of the mount Z axis transfer mechanism 35, the sealing lid 251 and also the aperture of the wide-mouthed piping part 232₁-232₁₂ of the reaction container 231₁-231₁₂ are joined.

In step S15, due to an instruction by the nucleic acid processing controller 63, the temperature controller 29 instructs a temperature control cycle by real-time PCR, such as a cycle in which the reaction container 231₁-231₁₂ is heated for five seconds at 96° C. and heated for 15 seconds at 60° C., to be repeated forty nine times for example.

In step S16, when temperature control at each cycle is started by the nucleic acid processing controller 63, the measurement control portion 61 determines the start of elongation reaction processing at each cycle, and instructs the continuous or intermittent movement of the measuring end 44, and therefore the measuring device 40. For the movement speed thereof, it is moved at a speed that is calculated based on the stable light receivable time and the number (twelve in this example) of exclusive regions 20₁-20₁₂. Consequently, the receiving of light from all twelve reaction containers 231₁-231₁₂ within the stable light receivable time becomes completed.

In step S17, the measurement control portion 61 determines the moment of each optical connection between the light guide portions 33₁-33₁₂ of the coupling ends 31₁-31₁₂ and the light guide portion 43 of the measuring end 44, and instructs the irradiation and the receiving of excitation light to the measuring device 40.

This measurement is executed with respect to cycles in which exponential amplification is performed, and an amplification curve is obtained based on the measurement, and various analyses are performed based on the amplification curve. At the time of the measurement, the measurement control portion 61 heats the heater 37 and prevents the condensation on the sealing lid 251, and a clear measurement can be performed. In a case where measurements are performed with respect to a plurality of types of target nucleic acids by real-time PCR, the measurement can be performed by executing using the measuring devices 401, 402, and 403 described in the third, the fourth, and the fifth exemplary embodiments in place of the measuring device 40.

Figure 12:
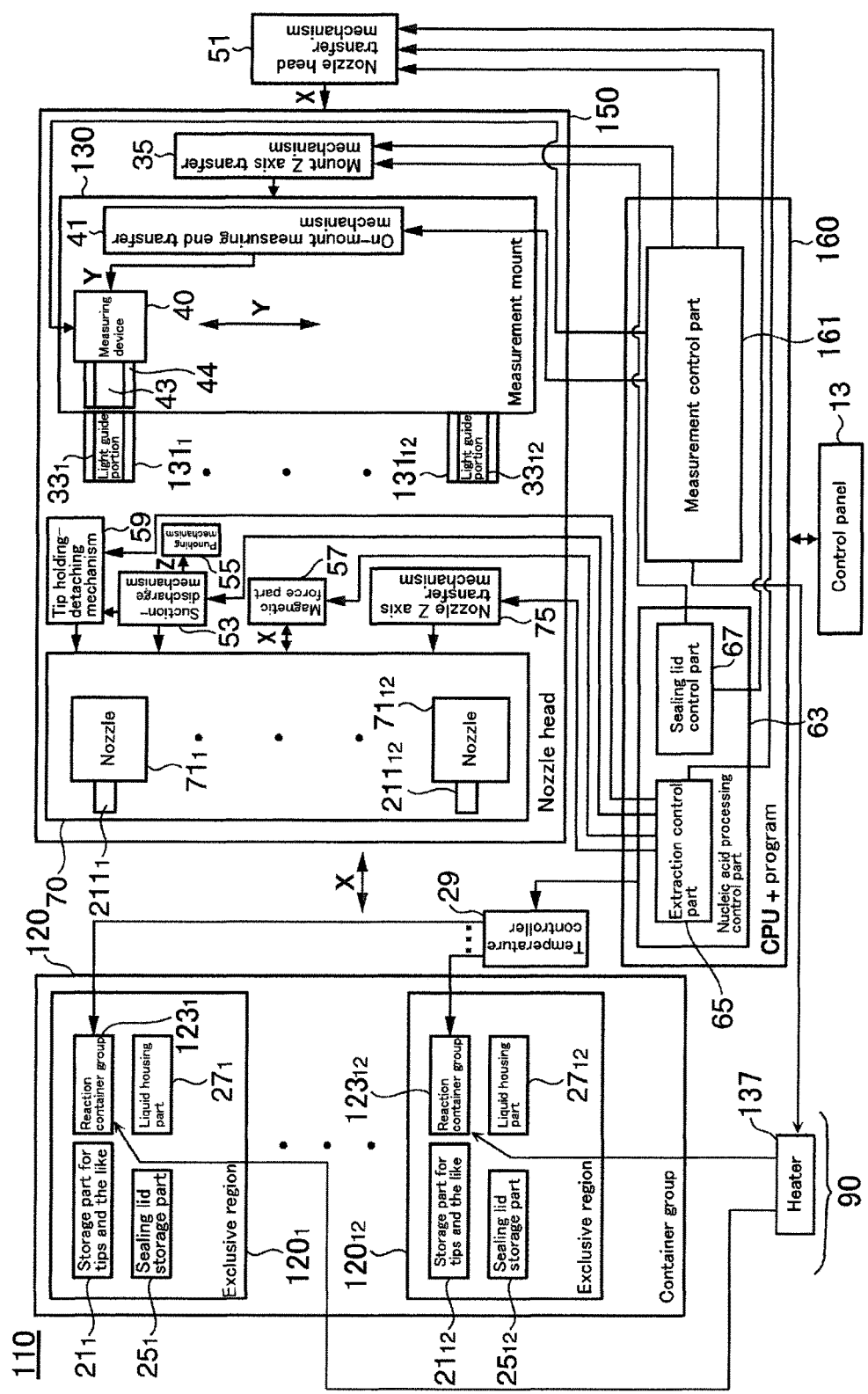
FIG. 12 is an overall block-diagram showing an automatic response/light measurement device according to a second embodiment of the present invention.

FIG. 12 is a block-diagram showing an automatic response/light measurement device 110 according to a second embodiment of the present invention.

Elements that are the same as the automatic response/light measurement device 10 of the first embodiment are represented by the same reference symbols, and the descriptions thereof are omitted.

The automatic response/light measurement device 110 according to the second embodiment differs from the automatic response/light measurement device 10 of the first embodiment in the respect that the nozzle head 150 thereof has a measurement mount 130 that is different from the measurement mount 30. Although the measurement mount 130 has a plurality (twelve in this example) of coupling ends $131_1$-$131_{12}$ having light guide portions $33_1$-$33_{12}$, which are simultaneously directly or indirectly joinable to the apertures of the reaction containers $231_1$-$231_{12}$ and optically connect with the interior of the joined reaction containers $231_1$-$231_{12}$, it differs from the measurement mount 30 in the respect that the heat source of the heater 137, which represents a heating portion for heating the coupling ends $131_1$-$131_{12}$, is not provided to the coupling ends $131_1$-$131_{12}$ provided to the measurement mount 130, or in the vicinity thereof.

The heat source of the heater 137 is provided to the container group 120 or the stage. The container group 120 is one in which twelve exclusive regions $120_1$-$120_{12}$, wherein the longitudinal direction thereof is along the X axis direction and storage parts are arranged in a single row form, are arranged in the Y axis direction for example. Each exclusive region $120_1$-$120_{12}$ has: a reaction container group $123_1$-$123_{12}$; a liquid housing part group $27_1$-$27_{12}$; a sealing lid storage part $25_1$-$25_{12}$ that houses a single sealing lid $251_1$-$251_{12}$ which has transparency, that is detachably mounted on the twelve coupling ends $131_1$-$131_{12}$ provided to the measurement mount 130; and housing parts for tips and the like $21_1$-$21_{12}$.

The reaction containers $123_1$-$123_{12}$, the temperature controller 29, and the heater 137 are included in a reaction container control system 90.

Figure 13:
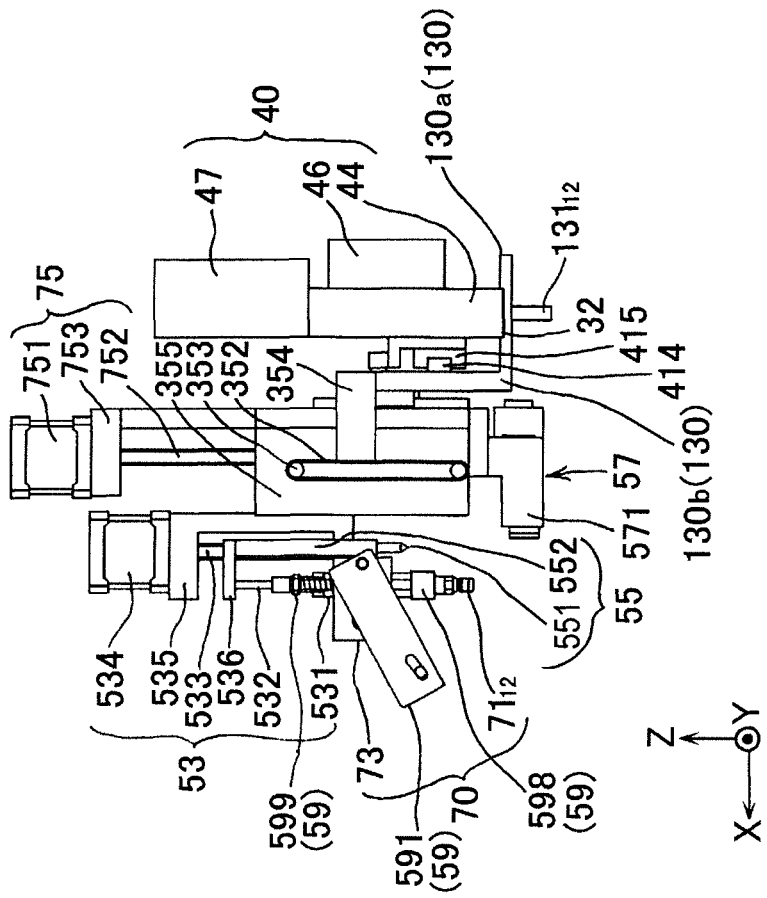
FIG. 13 is a side view showing enlarged, the whole nozzle head of the automatic response/light measurement device shown in FIG. 12.

FIG. 13 is a drawing showing a side view of the nozzle head 150. The nozzle head 150 is different from the nozzle head 50 according to the first embodiment in that the heater 137 is not provided to the measurement mount 130, and a heat source of the heater 137 is not provided to the coupling ends $131_{12}$.

FIG. 14A is a drawing showing a reaction container control system 901 according to a first exemplary embodiment of the second embodiment, and a state in which the coupling end $131_{12}$ of the measurement mount 130 is mounted on an aperture of the reaction container group which is provided with the plurality (twelve in this example) of reaction containers $231_{12}$ of the reaction container control system 901, and optical fibers 469 and 479 of a specific wavelength measuring device 404j for measuring light of a predetermined wavelength or wavelength band, which moves on a horizontal plate 130a of the measurement mount 130 while being supported by a vertical plate 130b, are connected to the coupling end $131_{12}$.

As shown in FIG. 14A, the reaction container control system 901 has: a reaction container $231_{12}$ that houses target solutions of DNA possessing a target base sequence and the like, and in which reactions such as amplification are performed; a temperature control block 294i of the temperature controller 29, which corresponds to the heat source and the temperature source of the heater 137i; and a heat insulating plate 295i provided between a container base plate, which has a heat insulating property, mounted with the plurality (twelve in this example) of reaction containers $231_{12}$, and the temperature control block 294i representing the heat source and the temperature source of the heater 137i.

The reaction container $231_{12}$ comprises a wide-mouthed piping part $232_{12}$ and a narrow-mouthed piping part $233_{12}$ provided on the lower side of the wide-mouthed piping part $232_{12}$ that is communicated with the wide-mouthed piping part $232_{12}$ and formed narrower than the wide-mouthed piping part $232_{12}$, wherein the sealing lid $252_{12}$ which has transparency, is fitted and mounted on the wide-mouthed piping part $232_{12}$, and the coupling end $131_{12}$ representing the member for light measurement is mounted on the sealing lid 252i.

The narrow-mouthed piping part $233_{12}$ has: a lower side wall section $233a_{12}$ provided such that the temperature control block 294 is making contact; and a band-shaped upper side wall section $233b_{12}$ positioned on the upper side leaving a spacing and, with the lower side wall section $233a_{12}$, sandwiching the heat insulating plate $295_{12}$, that is adjacently provided with the heat source of the heater $137_{12}$.

According to the present exemplary embodiment, by means of the instructions of the measurement control portion 161 (CPU+program 160), by controlling the heater $137_{12}$ according to the temperature control by the temperature controller 29 such that, in the case of PCR, the upper side wall section $233b_{12}$ is heated at a fixed temperature (100° C. for example) that is several degrees, or preferably approximately 5° C., higher than the maximum predetermined temperature (94° C. for example), the sealing lid $252_{12}$ fitted to the wide-mouthed piping part $232_{12}$ of the reaction container $231_{12}$ is heated and condensation on the sealing lid can be prevented. At that time, the upper side wall section $233b_{12}$ is separated by a predetermined spacing from the lower side wall section $233a_{12}$, in which the temperature control is performed, and the heat source is made to make contact with, or approach, and heat the upper side wall section $233b_{12}$, which has a smaller surface area than the lower side wall section. Therefore, the effect of heating on the upper side wall section $233b_{12}$ is that the sealing lid $252_{12}$ provided at a position in the vicinity of the upper side wall section $233b_{12}$ is heated, and the lower end surface of the sealing lid $252_{12}$ is heated, and condensation can be prevented.

On the other hand, since the coupling end $131_{12}$ is on the upper side of the sealing lid $252_{12}$, there is not nearly the effect of heating as for the sealing lid $252_{12}$. In the same manner, the lower side wall section $233a_{12}$ becomes temperature controlled at the predetermined temperature using a temperature source (e.g., a Peltier element having a cooling function, a heater, a cooling device, or the like) provided on the temperature control block $294_{12}$.

FIG. 14B is a cross-sectional view showing a reaction container control system 902 according to a second exemplary embodiment of the automatic response/light measurement device 110 according to the second embodiment.

The reaction container control system 902 is one in which a rod lens 430 is provided to the light guide portion $33_1$-$33_{12}$ of the coupling end $132_{12}$ as an example of an optical system element. Consequently, the optical state from the reaction container $231_{12}$ is captured with certainty, and excitation light can be uniformly irradiated into the reaction container.

Since the present exemplary embodiment is one in which the heater $137_{12}$ does not directly heat the coupling end $132_{12}$ and heats the sealing lid $252_{12}$ by heating the upper side wall section of the reaction container $231_{12}$, the effect of heating does not readily reach the coupling end $132_{12}$, and even if optical elements such as the rod lens 430 is built into the interior, the degradation or change in properties thereof, for example, is prevented, and measurements with a high reliability can be performed.

The foregoing embodiments have been specifically described in order to better understand the present invention, and they are in no way limiting of other embodiments. Therefore, modifications are possible within a scope that does not depart from the gist of the invention. The configurations, shapes, materials, arrangements, and amounts of the nozzles, the dispensing tips, the punching pin, the container group, the exclusive regions thereof, the storage parts, the measuring end, the measuring devices, the specific wavelength measuring devices, the suction-discharge mechanism, the transfer mechanism, the magnetic force part, the heating portion, the reaction container, the sealing lid, the measurement mount, the coupling end, the light guide portion, the nozzle head, the temperature controller, the heater, and the like, and the utilized reagents and samples are also in no way limited by the examples illustrated in the exemplary embodiments. Furthermore, although the nozzles were made to move with respect to the stage, it is possible to also move the stage with respect to the nozzles.

Furthermore, in the foregoing descriptions, although the amplification solution was sealed using a sealing lid for the sealing of the reaction container for PCR, it may be made such that, in its place or in combination, it is sealed using a sealing liquid, such as mineral oil. Moreover, in place of the punching pin, it is possible to perform punching by mounting a tip for punching on the nozzle. Although the plurality of specific wavelength measuring devices were joined by screw fastening both ends of a shaft that penetrates them, it is in no way limited to this, and they may also be joined by storing the plurality of specific wavelength measuring devices within a frame for example. Furthermore, the joining is in no way limited to an integrated case, and it is possible for the plurality of specific wavelength measuring devices or the measuring ends to be joined using a chain or in a chain form. Moreover, in the foregoing descriptions, although a real-time PCR measurement was described, it is in no way limited to this measurement, and it may also be applied to a variety of other measurements in which temperature control is performed. In the foregoing descriptions, although a case where the measuring device is provided to a dispensing device was described, it is not necessarily limited to this. Although a case where a measurement mount is used was described, it is also possible to not use a measurement mount and to directly and successively optically connect the reaction container and the light guide portions of the measuring ends of the plurality of specific wavelength measuring devices.

Furthermore, the devices described in the respective exemplary embodiments of the present invention, the components that form these devices, or the components that form these components, can be appropriately selected, and can be mutually combined by applying appropriate modifications. The spatial representations within the present application, such as "above", "below", "upper side", "lower side", "interior", "exterior", "X axis", "Y axis", and "Z axis" are for illustration only, and are in no way limiting of the specific spatial directions or arrangements of the construction.

INDUSTRIAL APPLICABILITY

The present invention is related to fields in which the processing, testing, and analysis of nucleic acids, which primarily includes DNA, RNA, mRNA, rRNA, and tRNA for example, is required, and is related to industrial fields, agricultural fields such as food, agricultural products, and fishery processing, chemical fields, pharmaceutical fields, health care fields such as hygiene, insurance, diseases, and genetics, and scientific fields such as biochemistry or biology for example. The present invention is, in particular, able to be used in processing and analysis that handles various nucleic acids, and the like, such as PCR and real-time PCR.

BRIEF DESCRIPTION OF THE REFERENCE SYMBOLS 10, 100, 110 Automatic response/light measurement device
20, 120 Container group
$20_1$-$20_{12}$, $120_1$-$120_{12}$ Exclusive regions
$211_1$-$211_{12}$ Dispensing tips
$231_1$-$231_{12}$ Reaction containers
30, 130 Measurement mount
$31_1$-$31_{12}$, $131_1$-$131_{12}$, $132_1$-$132_{12}$ Coupling ends
37, 137 Heater (heating portion)
40, $401_1$-$401_6$, $402_1$-$402_6$, $403_1$-$403_6$, $404_1$-$404_6$ (Specific wavelength) Measuring devices
44, 441, 442, 443 Measuring end
50, 150 Nozzle head
53 Suction-discharge mechanism
59 Tip holding-detaching mechanism
61, 161 Measurement control portion
70 Nozzle arrangement portion
$71_1$-$71_{12}$ Nozzles

What is claimed is:
1. A reaction container control system comprising:
a reaction container, including a lower side wall section, an upper side wall section positioned above the lower side wall section, and an aperture providing access to an interior of the reaction container, the reaction container including a wide-mouthed piping part defining an upper portion of the reaction container and having a diameter greater than the upper side wall section, the wide-mounted piping part including a vertically extending portion and a horizontally extending portion, the vertically extending portion having a length greater than the horizontally extending portion;
a sealing lid having transparency for sealing the reaction container by fitting to the aperture of the reaction container, the sealing lid having an upwardly extending sidewall with an outer surface and an inner surface and a bottom surface, wherein the outer surface of the sealing lid is fitted to the vertically extending portion of the wide-mouthed piping part of the reaction container and the outer surface of the sealing lid engages substantially all of the vertically extending portion of the wide-mouthed piping part of the reaction container, wherein the bottom surface of the sealing lid engages the horizontally extending portion of the wide-mouthed piping part of the reaction container, and wherein the inner surface of the sealing lid surrounds a coupling end optically connected to a wavelength measuring device, the coupling end engaging the sealing lid to facilitate wavelength measurements in the reaction container;
a temperature control block contacting and extending adjacent the lower side wall section of the reaction container, the temperature control block including a temperature source operable to control a temperature inside the reaction container;

a heater contacting and extending adjacent to the upper side wall section of the reaction container, the heater including a heat source operable to heat the upper side wall section, wherein the upwardly extending side wall of the sealing lid is located in a manner that prevents condensation on the sealing lid when the sealing lid is fitted to the aperture of the reaction container; and an insulating plate located between the temperature control block and the heater, the insulating plate contacting and extending adjacent the reaction container at a location between the upper side wall section and the lower side wall section, the insulating plate operating to thermally separate the upper side wall section from the lower side wall section.

2. The reaction container control system according to claim 1, wherein the reaction container comprises a narrow-mouthed piping part in which liquids are housable located below the wide-mouthed piping part and connected to the wide-mouthed piping part, the narrow-mouthed piping part being formed narrower than the wide-mouthed piping part, wherein the narrow-mouthed piping part is defined by the lower side wall section and the upper side wall section of the reaction container.

* * * * *

UNITED STATES PATENT AND TRADEMARK OFFICE
CERTIFICATE OF CORRECTION

PATENT NO. : 10,822,646 B2
APPLICATION NO. : 15/263483
DATED : November 3, 2020
INVENTOR(S) : Hideji Tajima Page 1 of 1

It is certified that error appears in the above-identified patent and that said Letters Patent is hereby corrected as shown below:

In the Claims

Column 38, Line 34-44 of Claim 1:
"...a reaction container, including a lower side wall section, an upper side wall section positioned above the lower side wall section, and an aperture providing access to an interior of the reaction container, the reaction container including a wide-mouthed piping part defining an upper portion of the reaction container and having a diameter greater than the upper side wall section, the wide-mounted piping part including a vertically extending portion and a horizontally extending portion, the vertically extending portion having a length greater than the horizontally extending portion;..."
Should instead read:
-- ...a reaction container, including a lower side wall section, an upper side wall section positioned above the lower side wall section, and an aperture providing access to an interior of the reaction container, the reaction container including a wide-mouthed piping part defining an upper portion of the reaction container and having a diameter greater than the upper side wall section, the wide-mouthed piping part including a vertically extending portion and a horizontally extending portion, the vertically extending portion having a length greater than the horizontally extending portion;... --

Signed and Sealed this
Fifth Day of January, 2021

Andrei Iancu
*Director of the United States Patent and Trademark Office*